(12) United States Patent
Michalowski et al.

(10) Patent No.: US 6,245,974 B1
(45) Date of Patent: Jun. 12, 2001

(54) MATRIX ATTACHMENT REGIONS

(75) Inventors: Susan Michalowski, Holly Springs; Steven Spiker, Raleigh, both of NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/122,400

(22) Filed: Jul. 24, 1998

Related U.S. Application Data
(60) Provisional application No. 60/066,118, filed on Aug. 6, 1997.

(51) Int. Cl.[7] .............................. A01H 5/00; C12N 15/85; C12N 5/14; C12N 5/11; C07H 21/04
(52) U.S. Cl. ...................... 800/317.3; 800/298; 800/314; 800/317; 435/320.1; 435/325; 435/410; 435/414; 435/419; 536/23.1; 536/24.1
(58) Field of Search .............................. 435/6, 69.1, 91.1, 435/91.4, 91.41, 440, 468, 470, 325, 410, 414, 419, 420, 425, 320.1; 536/23.1, 24.1, 24.3, 24.33; 800/293, 314, 295, 298, 317, 317.3

(56) References Cited

FOREIGN PATENT DOCUMENTS
| | | |
|---|---|---|
| WO 94 07902 | 4/1994 | (WO) . |
| WO 97 27207 | 7/1997 | (WO) . |

OTHER PUBLICATIONS

Allen et al.; High–Level Transgene Expression in Plant Cells: Effect of a Strong Scaffold Attachment Region from Tobacco, *The Plant Cell*:8:899–913 (1996).

*Journal of Cellular Biochemistry*, Keystone Symposia on Molecular & Cellular Biology, Supp 21B:167 (1995).

*Abstracts—4 th International Congress of Plant Molecular Biology*, Amsterdam, Jun. 19–24, 1994.

Boulikas et al.; A novel class of matrix attached regions (MARs) identified by random cloning and their implications in differentiation and carcinogenesis, *Int'l Journal of Oncology*:2:325–330 (1993).

Allen et al.; Scaffold Attachment Regions Increase Reporter Gene Expression in Stably Transformed Plant Cells, *The Plant Cell*:5:603–613 (1993).

Brylawski et al.; Association of Putative Origins of Replication with the Nuclear Matrix in Normal Human Fibroblasts[1], *Cancer Research*:53:3865–3868 (1993).

Forrester et al.; Dependence of Enhancer–Mediated Transcription of the Immunoglobulin Φ Gene on Nuclear Matrix Attachment Regions, *Science*:265:1221–1225 (1994).

Jarman et al.; Nuclear scaffold attachment sites in the human globin gene complexes, *The EMBO Journal*:vol. 7:11:3337–3344 (1988).

Kas et al.; Anchorage of the Chinese Hamster Dihydrofolate Reductase Gene to the Nuclear Scaffold Occurs in an Intragenic Region, *J. Mol. Biol.*:198:677–692 (1987).

Geest et al.; The β–phaseolin gene is flanked by matrix attachment regions, *The Plant Journal*:vol 6(3):413–423 (1994).

Cockerill et al.; Chromosomal Loop Anchorage of the Kappa Immunoglobulin Gene Occurs next to the Enhancer in a Region Containing Topoisomerase II Sites, *Cell*:44:273–282 (1986).

Hall et al.; Nuclear scaffolds and scaffold–attachment regions in higher plants, *Proc. Natl. Acad. Sci. USA*:88:9320–9324 (1991).

Hall et al.; Isolation and characterization of nuclear scaffold, *Plant Molecular Biol. Manual*:D2:1–12 (1994).

Phi–Van et al.; The matrix attachment regions of the chicken lysozyme gene co–map with the boundaries of the chromatin domain, *The EMBO Journal*:vol 7(3):655–664 (1988).

Levy–Wilson et al.; The Limits of the Dnase I–sensitive Domain of the Human Apolipoprotein B Gene coincide with Locations of Chromosomal Anchorage Loops and Define the 5' and 3' Boundaries of the Gene, *The J. of Biol. Chemistry*:264(35):21196–21204 (1989).

Gasser et al.; Cohabitation of Scaffold Binding Regions with Upstream/Enhancer Elements of Three Developmentally Regulated Genes of D. melanogaster, *Cell*:46:521–530 (1986).

*Primary Examiner*—John L. LeGuyader
*Assistant Examiner*—Mark L. Shibuya
(74) *Attorney, Agent, or Firm*—Myers Bigel Sibley & Sajovec

(57) ABSTRACT

Matrix attachment regions isolated from a higher plants, and DNA constructs and vectors containing such matrix attachment regions, are described. A method of identifying matrix attachment regions is provided.

19 Claims, 18 Drawing Sheets

Figure 1A:
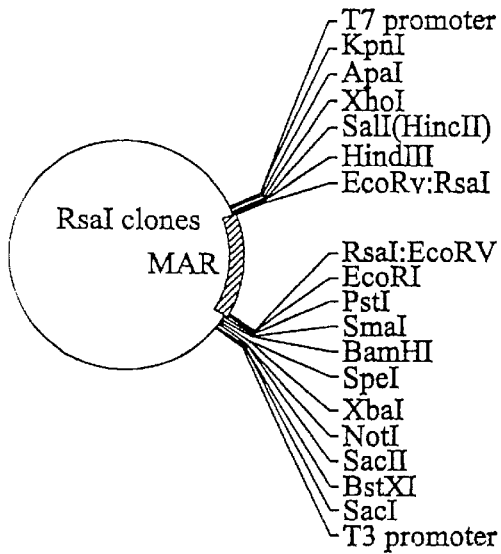
Figure 1B:
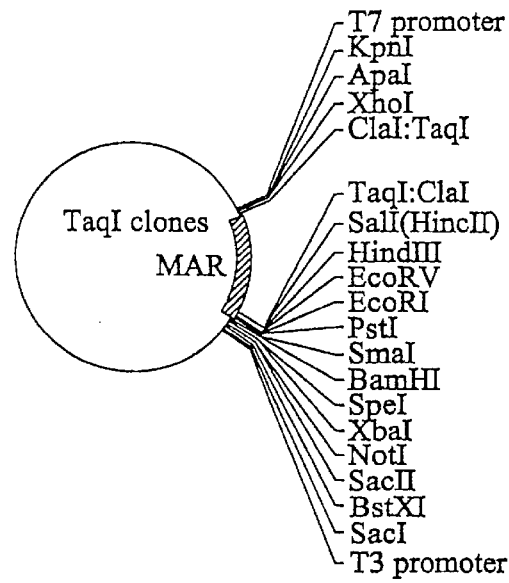
Figure 1C:
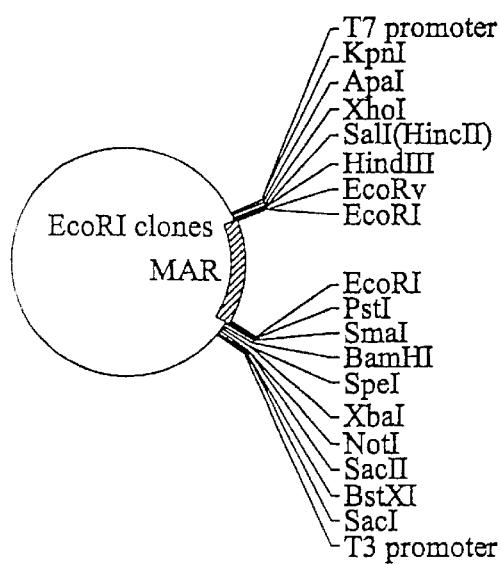
Figure 1D:
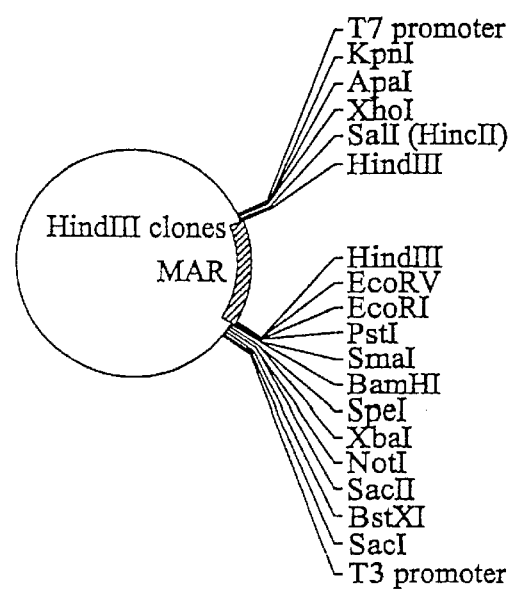
Figure 2C:
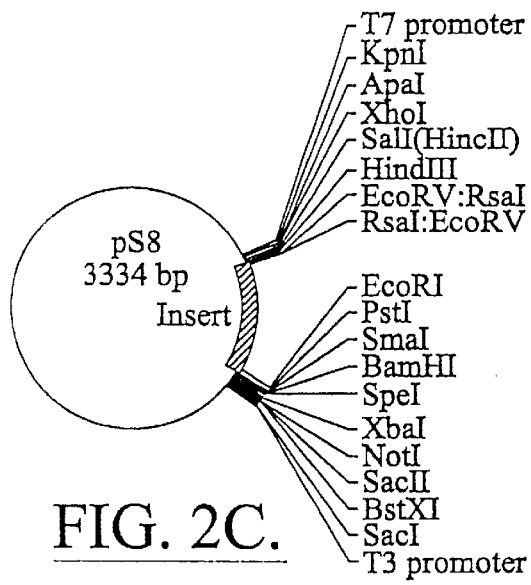
Figure 2D:
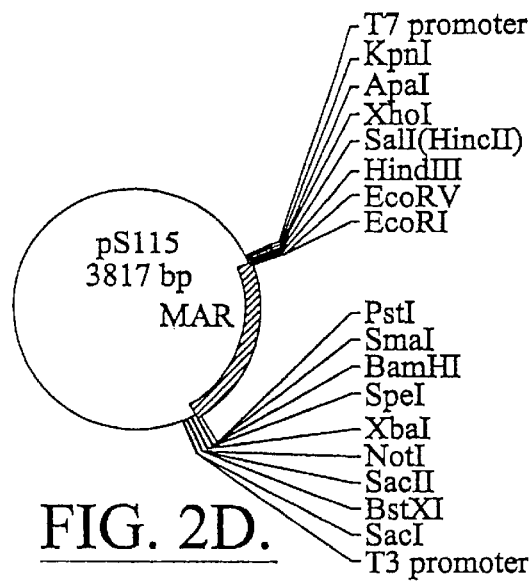
Figure 2E:
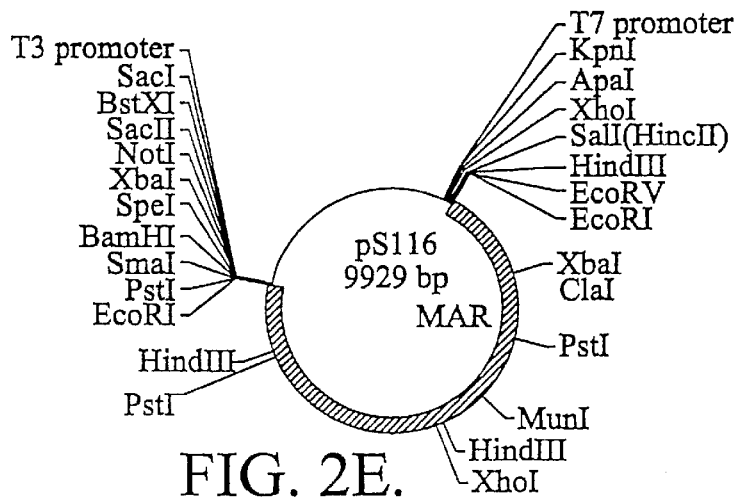
Figure 2F:
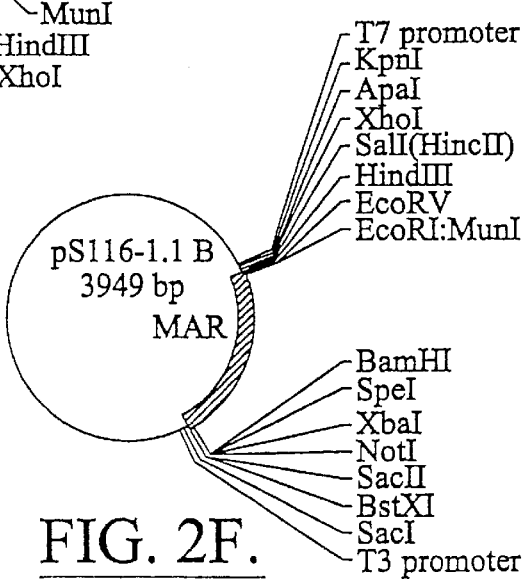
Figure 2V:
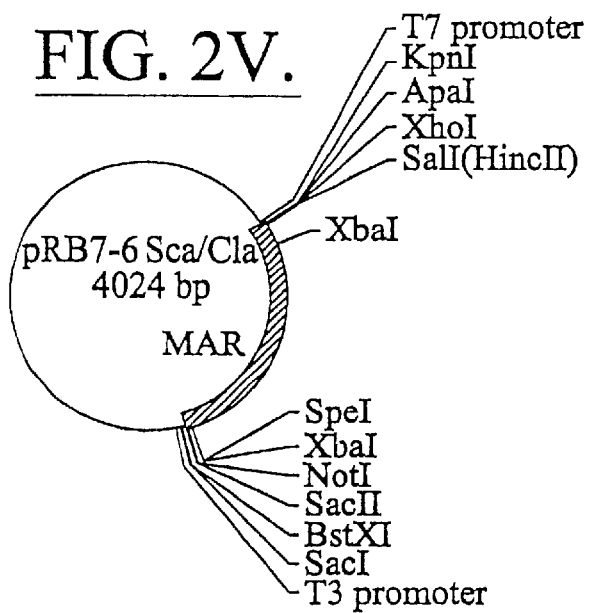

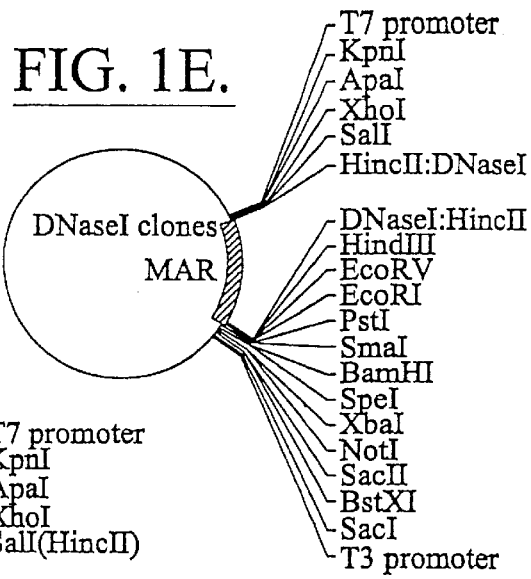
FIG. 1E.
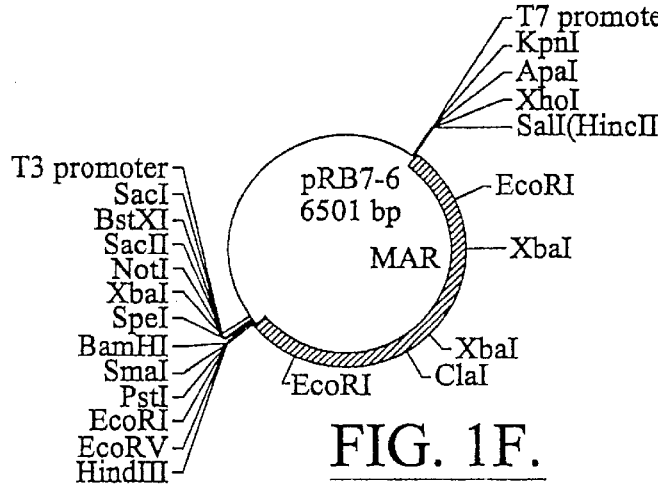
FIG. 1F.
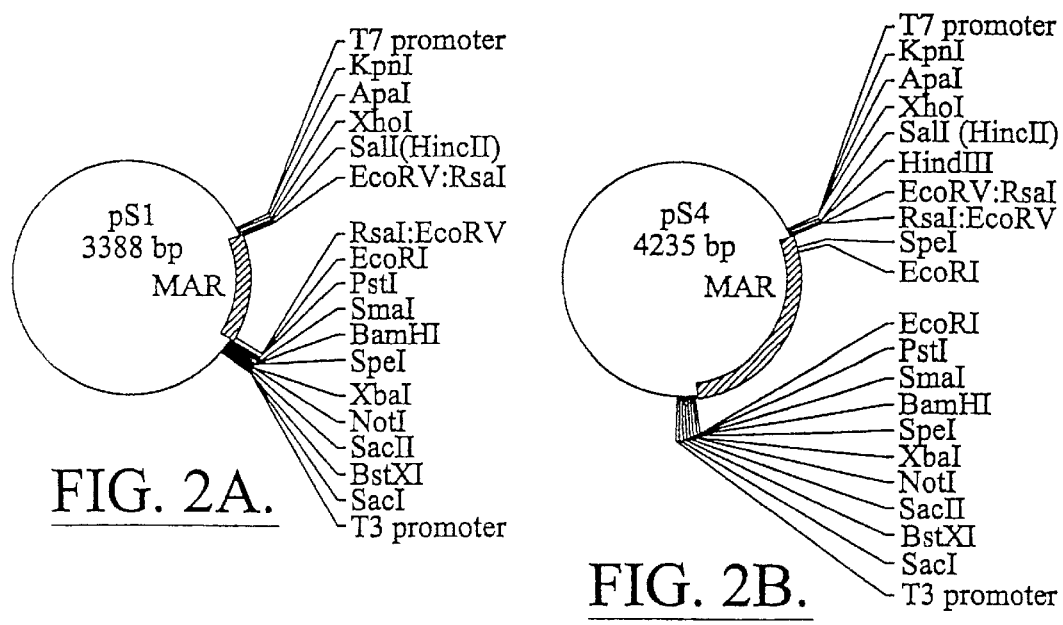
FIG. 2A.
FIG. 2B.

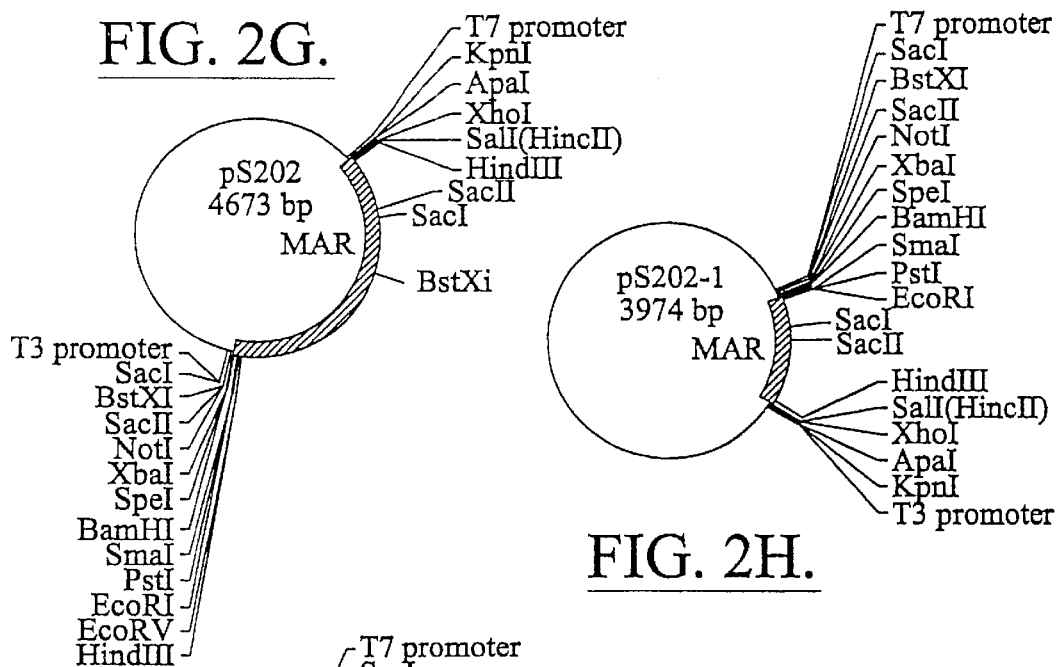
FIG. 2G.
FIG. 2H.
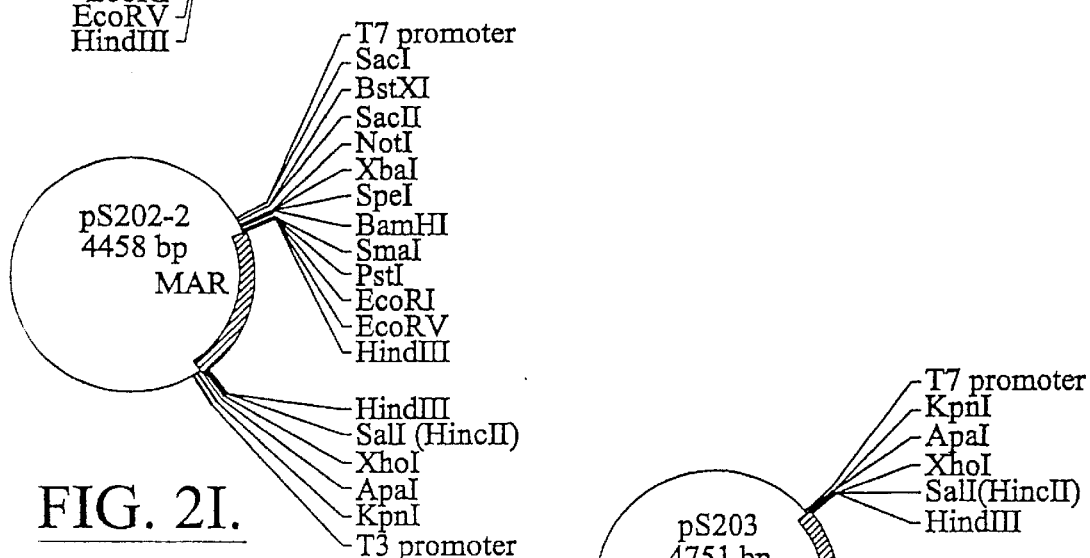
FIG. 2I.
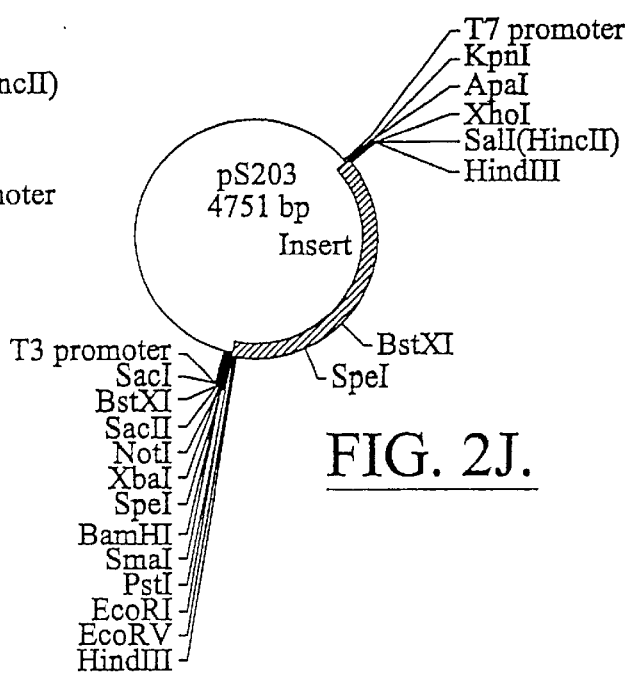
FIG. 2J.

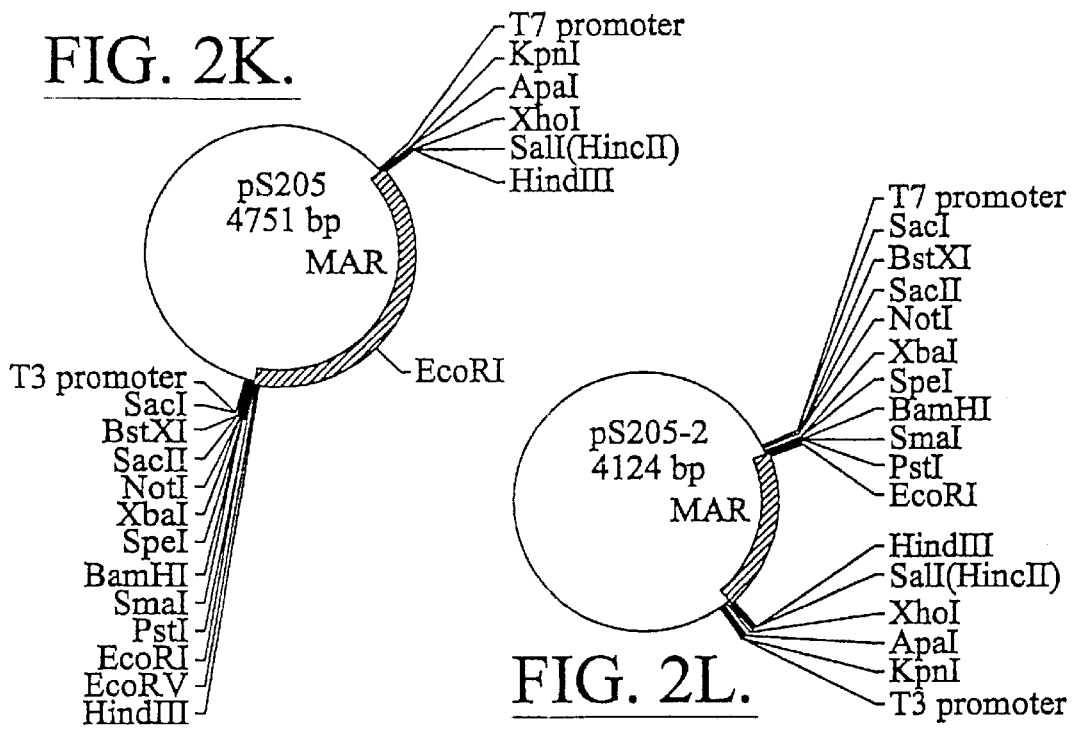
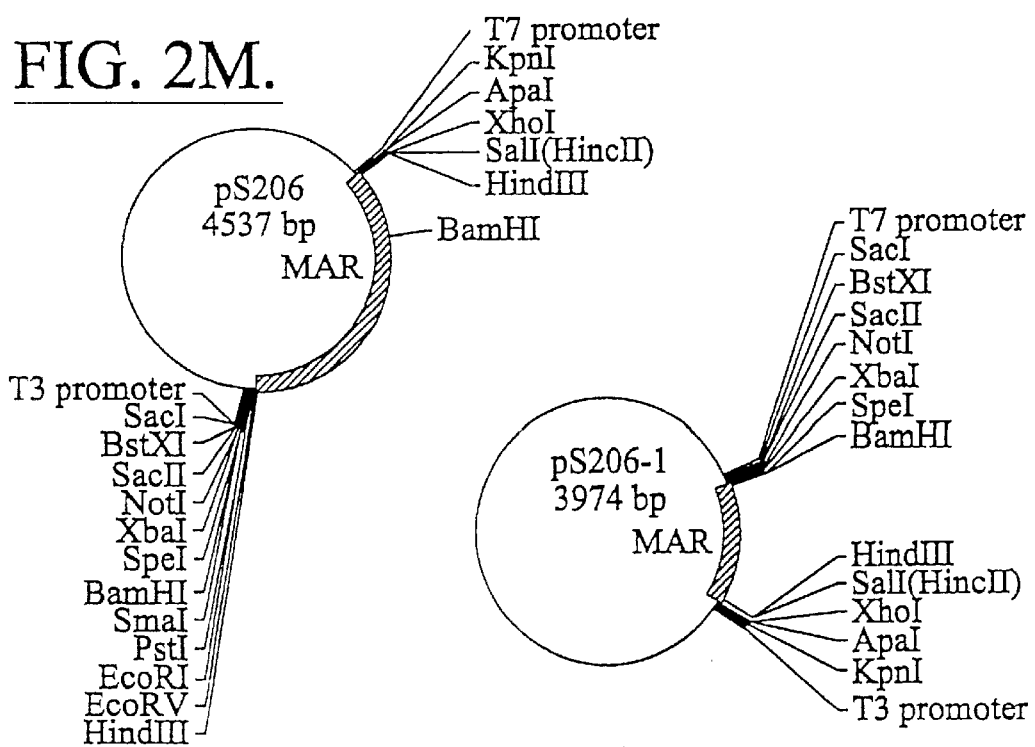

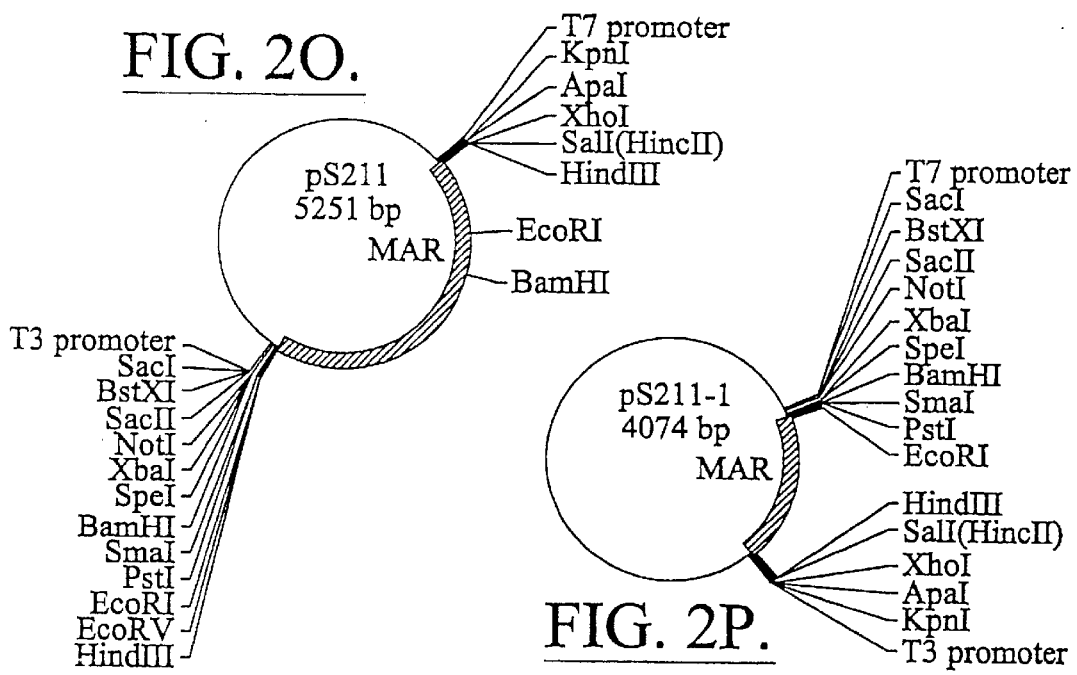
FIG. 2O.
FIG. 2P.
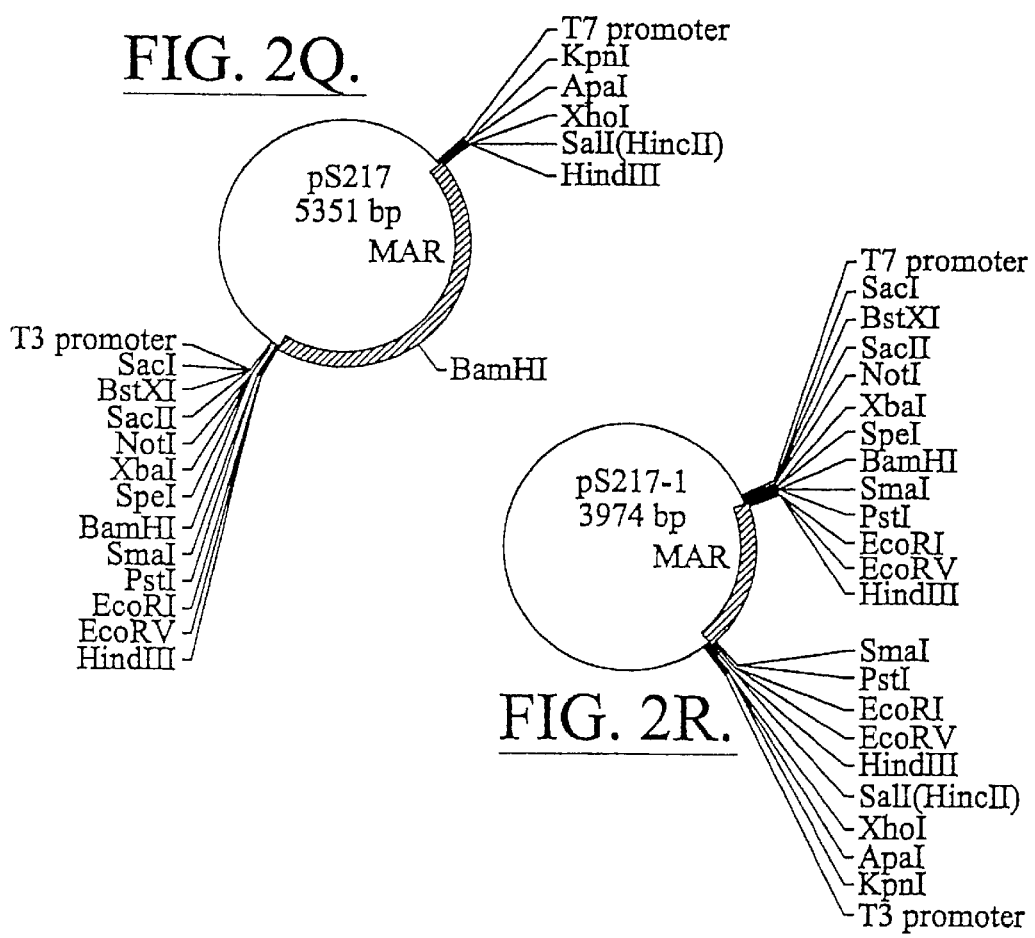
FIG. 2Q.
FIG. 2R.

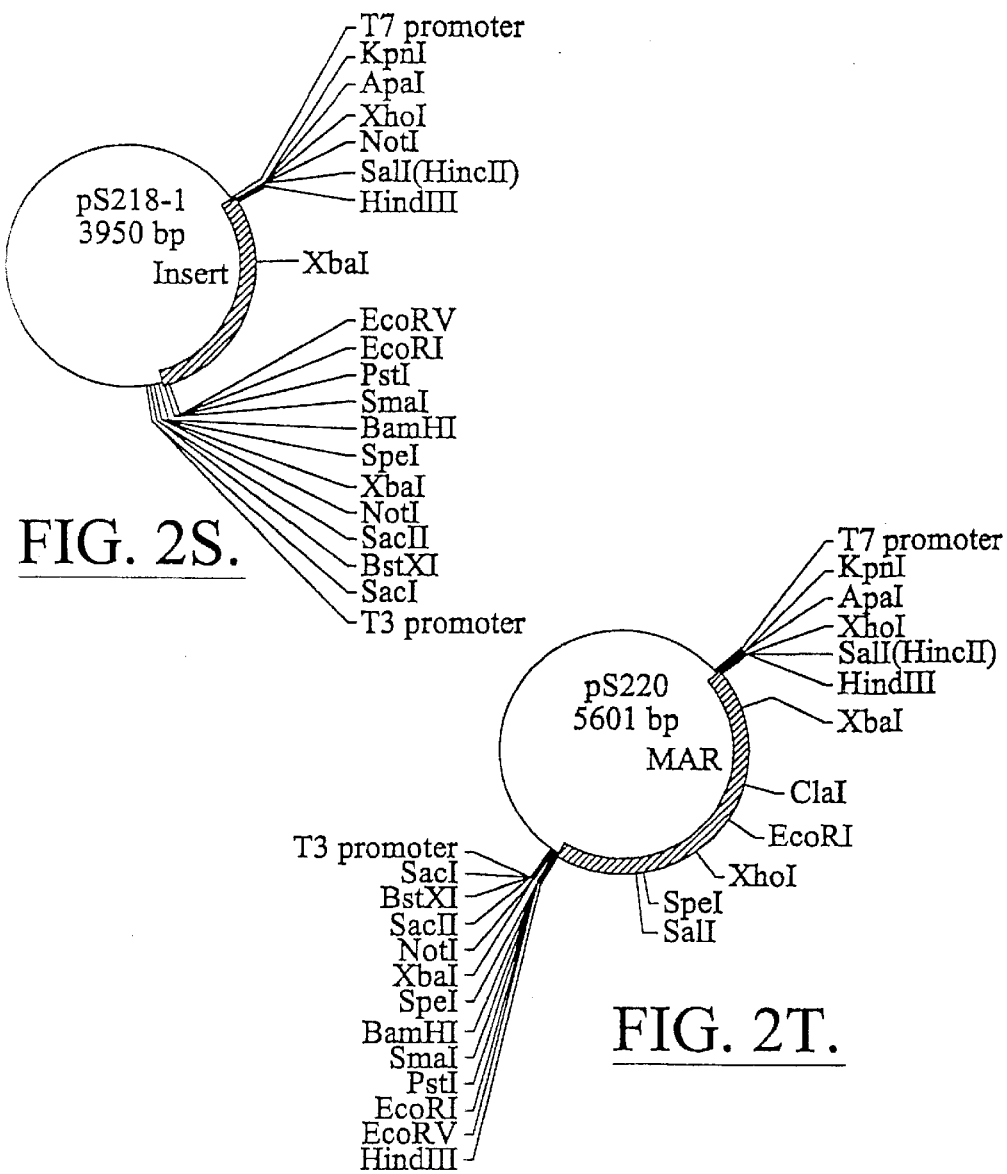
FIG. 2S.
FIG. 2T.
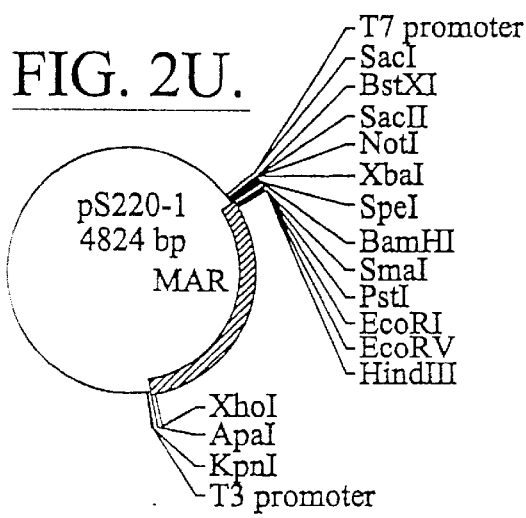
FIG. 2U.

pS1 (SEQ ID NO:1)

```
  1 GATACGTAAA CAACGTGTAT CCAGTAAGTA TCAAGCCTAA TCTCGAAGTG
 51 GTAGAGACGA GATGACCGAC TTTGACACTC ACTATGGGTC AATAATAATA
101 ACTGAAATAA AACTAAGATA TTTAAACCAA CATGATTTAC AGAATTTACA
151 ATAATTTATT TAATCAGCAG AAATAATCAA ATTTCTTCAA ATGTAACAAT
201 TCTCAATATA TTAATTAAAT TCCTTCAATT CAAATAATTT CTAATTTATC
251 AATTAAACCT CATTTACAGG AGTAACAATT AATTCCTTAA CAAGCAAGAA
301 TAATAATTCA TTAAATTCCA AGGATTTTTC AATTTATTAA TTAGCTTCAC
351 AACCTGAAAT AAATTATTAA AGTATCGTGT AATTATTATT ATTAAGCACG
401 ATTTCTGCCG AGGACATACG GCCCGATCCA GAGTATC
``` pS4 (SEQ ID NO:2)

```
  1 GATACTAGAG TGGTGTTATC AATTCTTACT CGTATGAATT AATTAAATTT
 51 GTCTCTTATT TCTGTCCTAA GTCATATACA AGAAATGCTA ACTCCATCCG
101 TTTCAATCCC TATGACATAG TTTGATTTGA TTGAATTTGA AAATTTAAGA
151 AACAAAAGAT AATTTTTGTG ACTCATAATT TAGACATGTG TTATAAGACT
201 TTTCTCATGA ATTTTTTAGA AACAAATGAT AATTTTTGGA ACTCATAATT
251 TAGACGTTTT ATAAAAAATA CTAACTGCAT CTGGTTCAAT ATTTATGTGT
301 TATTCCTATA AAACTTCTGG ACTTATATTT TTAAATATTT CATAATATTT
351 GGTATCGGTA TAATTTTTTT GTCACTTTTG GATGAAAGGG AAGTTTAAGT
401 AAATTTCTTT TTCCAAATTT AGAAAGTTAT AATATTCTTT TTAAAACGCC
451 CAAAAAGAAA AATAAGCTAT TGATTATTAT AAGCCTAAAC CAAAAGAATT
501 CTTTGACTAG TAGGAAGCCA TTTTTAAGTT AGGCGCCAAA ATTCAAAGCC
551 AACGTGGGCA TATCTCCAAA CTGGCGGCTA CAGTATC
``` pS8 (SEQ ID NO:3)

```
  1 ACCGCTTTTA TTATTATTAT TTTTACCGAG AATTACAACA TCATGAAAAT
 51 ACATCTCGAA CCACGTCACA TCAATGCACC CGCGGTTATT GACATATTTC
101 AACTCTGTTG AGATTTGGAT TTGGGTCACA TAAATGTGCA CCCGAGTTTA
151 AGAGGATAAC ATTATTAAAT ACGCGCCTAA AACGACTAGC GTATCATTAT
201 TTTGGGTAGG GCCGTGAAAT TTTGCTAAAC TGCCCATCCA GAAATCTAAG
251 TAATTTTACC AACACGTATA GAGGGCCCCA CAGCTTGTGT ATTTTTGTTT
301 GTCGAGGCTC GTCTCATTCA TTATTTTTAA AAGGAATTTG CAACGTCGTG
351 GAAATGCATC TCGAACCACG TCACAATCAA TGA
```

FIG. 3.

pS115 (SEQ ID NO:4)
```
  1 GAATTCGATA GACTCACTTA AATATTAGAA GTGAATTACC TAGAGTTAGA
 51 TCCAAAACAA TTATCTTGCA CCTATCCTAT CAACCCTTAT CTTTTCCCAT
101 TGATTACTAC CTTGCTTACC TTTGTTACGA TTTTCATTAG ACAATAACTT
151 TAGATTCTTA GTTAATTGCA GTTAGAAATT ATATTAAATT TCAATTGTTG
201 GATCATCTTG AATACCAATC AAGCTAGAAA ATACAAGAAT ACTGTTTAAA
251 TCAAATCCAT GTGGATACGA TATTATACTA TATTATATTT GACTTGTGAG
301 CATTATTTAT GTGTGTTTTG TGCTCGTCAA AGTTTGGCGT CGTTGCCGAG
351 GATTGGCAAT CAATAGTGTT TGAAATAGTT TTTGGTGCTA ATTTAGGAAT
401 TAGGTTTTAT TTATTTATTT TTTCTTTTCT TTTCTTTTTC CTTTTCTATT
451 TTATTTCCTT TATTAGTTAA CTTCTTTTCA AGATTTTTTT TGTAGTACCT
501 AACAAGTTAG AGAAGATACT GTAGATTTTG AACTCTAAAT GTTGTGAAGA
551 TGGAGTACAA CCAGCCTAAG AAAATATTTG AATAGTTAGC AGCTGAACAT
601 TATCGGCGGT CGGTTATGCG GTTTAAATGC GGTGGAAGCA TCTACCACCG
651 CAGCCTAAAG AAAATATTTT GAATAGTTAG CAGCTTGAAC ATTATCGGCG
701 GTCGGTTATG TGTTTTAAAT GCGGTGGAAA TCATCTACGG GCTAACTGTC
751 AAGCAGGTAT GTATTCTTCC TATGGTTCGT ATTTTGAGGA GTCTCACTCT
801 GTTTCTAGTT CGTACATGTA TGAGGATTCA TATGGGCACA ACTCTGACTC
851 TGGTTGGGAT GAATTC
``` pS116-1.1B (SEQ ID NO:5)
```
  1 GAATTGTATT ATTGTTAGGT GGGAGAGATT TTTGACTATA TGGGTTAAAA
 51 TCAGCGACAA AGGGCCAAAT ATACCTATTT ACTTTTAAAA ATAGTCTAAT
101 AATACCTCTC GTTATATTAT TAGGTTATCT ATACCTTTGC AGTCATATTT
151 TGGGTTCAAA TATACCCCTC ATTTAAACGG AGGGACACGT GTCATCGTCC
201 TGTTGGTCAA TTCTAAATAT CTCCTAATTA ATTAAAAAGA CTCATTACCC
251 ATATCCGAAA AATATTTTTT AAAGCAATAT TTTTTTATAA AAAATGGAAA
301 AACTGAAATT ATTTTTACTA AAAATTGAAA AAAACGAAAA TAGTTTTTTT
351 TCAGTTTTTA CAAAAAAACT ATTTTAGAAA AAATTGAAAA ATATTTTCTA
401 AAACAATGTT TTTGTAAAAA CTGAAAAAAA AGAAGCTGAA AATCAATTTT
451 CTAAAGCAAT TTTATTTGTA AAATCTGGAA AAAACTACTA AAAACTGAAA
501 AAATGAAAAT ATTTTTTTTT CTAATTTTTA CAAAAAAAAC TGCTTTAAAA
551 AAAGCTGAAA ATATTTTCTA AAACAATATT TTTGTAAAAA CTAAAAAAAA
601 AATATTTTCT TCTTTTTTTC AGTTTTTAGT TAAAAATATT TAAGTTTTTT
651 CCAGTTTTTA ATTACTTTAG AAAATTACTT TTCTGCTTTT TTTTCAGTTT
701 TTACAAAAAT ATTATTTTAG AAAATATTTT TCAGTTCTTT AAAGCAGTTT
751 TTTTTTGTAA AAACTTGAAA AACAATATTT TCGTTTTTTT CAGTTTTTAG
801 TAAAATTTGT TTTTAGTTTT TTTCAGTTTT TACCAAAAAT AAAATTGCTT
851 TAGAAAATTA TTTTTCGGGT ATGGGTAATG GGTCTTTTTA ATTAATTAGG
901 AGATATTTTG AATTGATCAA TAGGACGATG ACACATGTCC CTCCGTTTAA
951 ATGAGGTGTA TATTTGAATC CAAAGTAAGA CTGCAGCCCG GGGGATCC
```

FIG. 3. (continued)

pS202-1 (SEQ ID NO:6)

```
  1 GAATTCGATA TGGCTTGTTG GACAAGAATT AATGAATCAA TTGTGAAAAA
 51 GTTGATGGAC ATATTGAAGG TAAAATCATA TACTATTTTT CTAAAATCTC
101 TTTTAAATGT TCCCCAATTA TCTGATTTCT ATATTGCTCT TAAATGTCAC
151 TCAACCTTAG ATCAACAAAC ATATAACTTA CCCAGTACAT AAGAGATTGC
201 GGCATTATGG CTTGAAGAAA ATCCTAGAGA CACATCTGCA CCACATATTT
251 GAATTTATAC CCACAGTAAT AGAGCTCGGT TAGTACATTA TTATTATGGA
301 TGTTACGATC CGTTGCAGTA TCCATTATTA TTTTCCTTCG GTGAAAATGG
351 ATGACATTGT GGAATTAAAA AAATTATTCA GACAAAAAAT TCGACGAAAC
401 GTAGAGCTTA CTGCGAACAT GAACAATTGC CCAGTATATC AAATACGTGT
451 TCAGTTGATG GATTCCTTGA TATGGAAGAT GAATCACTAC AAAGAGGAAA
501 ACGAAAAAGA GATACAGTGT CTTGTCGAGA GTATTATTGT TACAAATTTC
551 AACTAAGAAA TAATGAAACA AATGAAGTGT TACATTGTGG GAGAATATTC
601 CAACAATTTA TAGTAGATAT ATATATATAA AGCTT
``` pS202-2 (SEQ ID NO:7)

```
   1 AAGCTTGCAC GCCTACATCG TGGGATAATT TAGAAAAAGG AAAGGGTATA
  51 TTGGATCCCC CTATCATTTG TGAAACAGGT AACCATACGA GAACCCCTTT
 101 CGCTTCCTGA AAAATGTTAT ATATTGTTGT ACTCATATTT ATACACTATT
 151 TATTATTAAT ATAACGATGC TTATTTTGCT TGGAGATTGG AGATTATCAC
 201 AGCTTATTTA TCTTATATTG TATCTTATTA AACTTAAAAA CATAAATACT
 251 ACGTGCTCTT TTAATTTGGG ATCTATTAAG GGTTCGTTGC ACGCTTTTAA
 301 ACATCTTGGC TATTCTGTTT ACCAGCTGCT ACCTTAGCCT GTATGCTTAC
 351 ATCATCTCCT AATTTAGACA AAGGAAAGGG TATATTGGAC CCCCCCTATC
 401 ATTCGTGAAA CAGGTAAACA TACATTCAGA TTATACTCTT TTCAGAATGA
 451 CATATTGTTT ATACATTACT GTAAATTGTG ACTATTTGTA TATTAGGGTC
 501 CACATCGGGT ACATCTAACC TGCGTCATGT TATCTTGAAC ACTGTTCCAA
 551 TCAAAGGTTT GCACAAACTT AATGTTACAA TCATGTCCAC CATACGTATG
 601 CCTTGGTGCT CTTTTTTTTC CTAATGATAC TTCTTATATA TTCAGCTCAT
 651 AGGCGGGCCA GAAAGGTGTG CCTGGTCACT AAAGAGCAAC GAAGTGAGTA
 701 TGTTGCTCTA AAAAGGGTCC CACACTGTCA ATTCTGTCAT CCAAAGAAGT
 751 TTGAATATGA ACCTCCAGGA TTTTGCTGTA ACAGTGGTTC AATAAGGTTG
 801 ACATCTCATA AAATGCCAAC TGAATTATCG GAGTTATACT TTGGAAATAC
 851 TGAAGAATCT GAAAATTTTC GAACTTATAT TAGAACATAC AATAACATGT
 901 TTGCATTTAC TTCACTTGGT GTCAAGTATG ATAAAGAGCT AGCGAGAAGA
 951 AATTGTGGTA TCTACACATT TAGAGTCCAG GGACAGATGT ATCATTTTAT
1001 AGATGATTTA GTTCCTTCCA ATGAAAAACC TAGGAATTTA TAGCTGTACT
1051 TCTACGATAA TGATAATGAA CTAGCCAAAT CAAGCTT
```

FIG. 3. (continued)

pS205-2 (SEQ ID NO:8)

```
  1 GAATTCTTCA GCCATTGTAC ATATAGTTGT GTATTAATGT TATTAATAAT
 51 GGATAATTAA ATATATACCT GGAATAAATA TACGATATTA TAATAGTGTG
101 TAATTATATA TAAAAATTAT ACATAATATA ATGATGGTAT TTAATATAGC
151 ATAAATTTGA ACGATCTGGA TTGATTTCTT GAATCAAAAT AGAGTTGTGT
201 GAAAAGAAAA GAATGAGATG AAAAGCAAAG TATGAAGAGA TGAATTTGTG
251 TTTTTTTTAT GGAGGAGGAA GGTTCTCAGT GATGGAATCA TCCCTGGTTT
301 TCTTTAGCAC CAATGAAAGT AATGAACCCC CCCCAAAAAA AAAAAAAAAA
351 AAAAAAAAGG GAGAGAGAGT AGAATGGAAC GGCTAGGTGA AAGTATAGGA
401 GTAGAAATTA GGTTCAGGGA GAGAAAAGGG GGGAAATTAA TTCCTAAATT
451 AATGGGATTC TAATTTTTAA ACTGTTTTGA AATATTTTAA AAGTAGTGTT
501 ATTTATATTA TTAACTTTTA AAAAAAGTCA AACGAGGTAA AAATTCCATG
551 GGGGAAAATT TAAATGGTTA GTCTTCTATA ATATTTTCAA CTCTGCTTAG
601 CACTAAAAAT TAGTCTAAAA ATAACCCTAA ATTAGTGTAT CTAAATTAAT
651 TAGTTCATCG AACAGGAGCA TTGGATTATC CCTCCAGAGT TACACAGGAA
701 GCTT
``` pS206-1 (SEQ ID NO:9)

```
  1 GGATCCAGCT ATTATTATAG CATGTGAGTT GTCCGTGAAC AGCTAATTTT
 51 TTACCACACC CAAATTCAAT ACTATTTTAG TGTAAATATA TCTTTTAGGT
101 CTAGTCTTAA TATTTAACTT TTTGTCTTAC TTTTAATAGA TTTTATTTGA
151 GAAAAATTAA TAATTACAAA AAATAAAAAG TATATATTCA CATACTTATA
201 GTACAAACTT TGTTTCTATT TATAAAGAGA AAAAGAAATT TTACAAAAAA
251 CAAATATATT TGCTTTCTTT TAATTAGTAG TTTTATTAAG CAAGCTATAG
301 AAGCTC
``` pS211-1 (SEQ ID NO:10)

```
  1 GAATTCCGTG GTTTTAGCAC GGTCGCTCAA TTGTCATATT TGGCTCATTT
 51 ATCTGATTTT TAAACAATTA AGAACTTATA TGCAAATTTA ACTTTTAAAA
101 CCGCTTTTAT CATTATTTAT TTTATACAAA ATTACAACGT CGTGAAAAGG
151 CATCTCGAAC CACGCCACAA CCAGTGCACA CGTGATTTGT TGACGCATTT
201 TGGACTTCGT CAAGATCGTG ATTTGGGTTA CATAAATGTA CACCCCGTAT
251 TTAAGAAAAT AACCTTATTA AATATTGCGC CAAAATACTA CGCGTTATGA
301 TACTATTAGG GTAGGCTTGT GAATTTTACT AAATCGCCCA TCTCGGAATC
351 TAGGTATTTT CTTATATTAA AAAAAATAAG ATGGGGGCCT GCAATTTTTT
401 ATTATTTAAT ATTTATTTAT TTTTTAGCGA AGATCCCTCC CTTATTTTAT
451 GAATACCCTT TAATGACTAC ATCTTTATTA TTACTAAGTT TGTCTATAAT
501 TATGAAGTCA ATCTCTACAT ACATAAAAAT AACATATTAA TTACTAATTT
551 AAAACAAATA TTAATGGAAA GTAATATTAC TAAAATTATA ATTACAAACA
601 ACATGGAATT GTCACAAAAT AAAAAATAAA AACTAATTAT CCCATAGTTG
651 GATTAAAATT CATATTGTTA GTATGACTTA AGCTT
```

FIG. 3. (continued)

pS217-1 (SEQ ID NO:11)

```
  1 AAGCTTTAAA AGGAAGAGAG CCACAATTTT CTTTGACCTT CCTTCTCTCC
 51 TAGCCACTAA GATATACAGT ACTGGTCAAA AAGAGCATAT TTATAGCTCA
101 AAATTTTGCC TTTTTCTGTT GTAAACGTGA TTGTTTCTTA CTTGGATTCT
151 TGTTCTATAT ATTTACGGGA GAAAAGAGCA ATTTGCATGC TCCTAAATCT
201 TTTATTTTCT GGTGAAAAAT TGGTCTTTAA TTGGCTGGGA ATTATTTTTT
251 AGATGCTACA ACCTTGACAA ACACCTAAGA ATATTTTAGT GACAATGGCT
301 TGTTCTTTGA GTACTGGTTT TTCTGTTTCT GGTCCCTGTT TCAACGCCAC
351 AGCCAAAGAG TCTCGTCGTC ATTGCCCTTC GATTGGCACT CTGCAACTTA
401 AAGATTTAGC ATCCAGAGAA TTTCTAGGCA AACCCTTGGA TTATGCATCA
451 GATCATATTG GTACTAACCA TTGGAATGTT GAACGACTTT CTGTATGTAA
501 ATCTCTGATA CATTTGCTTC TGTGTTTATA CTTGGTGTTT TCATGTTTTC
551 ATTCTTGTTT TAAATTTTTC GAGATCAAAT CATTTATAAG TATTTATTCT
601 AATGATTTTA GGCACAAGTA TCAATCGCTG CTCAGAGATG GTGGGAGAAG
651 ACCCTTAAAC CCAACATGGT AGAGATCAAT TCAGCAACAC AACTTGTTGA
701 TTCATTATTA AAAGCTGGTA ATAGATTGGT CATAATTGAC TTCTTCTCTC
751 CTAGCTGTAG AGGTTTCAAG ACTTTACATC CTAAGGTAAG ATATATAGCA
801 ATCCCCTAAA AAAAAAAAAA AAAAAAAAAA AAACCAACAA CTACATCGTA
851 ATCCTAAGCA AGTTAGGGTT AACTATATGA ATCATCACTA GACGGATCC
``` pS218 (SEQ ID NO:12)

```
  1 AAGCTTAACT TTACTCACAT TGCTTTCTTT AGGGAAGCGT CTTCTTAAAT
 51 GACCATCCTC TAAATTTCTC ATGAATCTTC TTCTGTTGTC CACTCTGTTA
101 TCGCTGAAAC GAAATCTGAA ATTGTCATGA TGCTGACTAT TATCCAATCA
151 CTCAGTCTCT AATTCATATT TAGATTATCT TGTTCACCAG CCCATACTGA
201 TTTTTATTGT TTTGGGGTCT AACTTTTCCT TCCGGTAGTC GGTTGGAGTC
251 ATGAACTTAT TTCTTGAAAT GAGGATATGA CTTTATGGCC TATACTCTTT
301 TGGTGTCTCA AGGCCTGTCA CCTCTCATCT TTTCCTTCAA TTGACTATAG
351 ACTCTGTAAT ACTGTCATCT TTGGGATCTA CCGTTGTCCT CCATGTATCA
401 TATCTTACTC ATAATGCTTC ATTAACTATT TTCTTATTTC CCGCTAACAT
451 TTATGTCTAT CACTTTATTC TGAAAACTCG AACAAGACAT TCTTTTCGTT
501 TTAGATCCCC TTTGCTCCAT CCAGTGGTTC TTCGGGGGAC TTAACGTTCT
551 CGCTCTCCTA GGGAGGCGAG CCACACTAAG GTAATATTTA TCCCTTCTAG
601 GCTTTCCGTG CCTATCTTCT GAGATATTTT TTTCATGCTA ATATTCACAT
651 CTAATTGTAA TTTTCTAGAG TGCGCCATCT GGGTGCCTCA CAAGAAGAGC
701 TATTAGCATC TTTGTAATAT CCTTCGGAAA TGTCAACTAA CACAACACAA
751 TCCATTCACC ATTTTGGGTT ACTCTAACCT CAGTCGGATA CTAATATCCT
801 GTCATTTTAT TAAACTACAC ATGTTAGCCC CCAATAGGAT ATAACTAAGA
851 TGGGTGTGGC CAATTCTACA TACATCTGTT ACTGTTGAAA GTAAGTCGCA
901 ATGCTTTTAT TTTTCTGCCG GAGTTGAAAA TACCGATAAT CTATATTAAC
951 TGGGTACCTC GTACCCTTCT CATCTTTCTC CTTTTACTTG TTGAAGCTT
```

FIG. 3. (continued)

pS220-1 (SEQ ID NO:13)

```
   1 AAGCTTGAAA AAGAAGAATT AAGGCTTGCT TTCTTAATTT TTAAAAAATA
  51 AAAATTATTT TGAACTATCT ATACTATATT AAAAGCACGA AACCCTATC
 101 GAAATGTCGT TCGCCTTTTT TACCCTTTAA AAATAATTTT ACATTAGACA
 151 AAATAGTCAT TTTACTATTT TTCCTAATAT ATAGGATTTT AAAATTAATT
 201 TAACTTTGGC TATTAAACAT TTTCTTATAA CTTGAAATAT GTAAAACTCC
 251 TAATATTTAG AAATTTAATT AACATAACCA AGGATTTTTA TATCGGTAAT
 301 AACTCTAATA TGGTATCCAA ATCAGTCTAG AACTCTCTTA CCTCTAATAA
 351 GTAAAAGTAC TTCTAATAAA TTCATATACT TTTTCTCTCT TCTCCGATCT
 401 CTCTTTGCTC TTCTTTTTAT GTATCCTTTC CTTTCTAATA GCCTTTTATG
 451 AGAAGTAAAC TTTTAGGGTT GGCCCCCCCT CCCCCCACAA TTATATAGTT
 501 TCTTACTCAG TTGTTGGAAT ATAATTCAAA TTCTTAAATA ATTGACGGTG
 551 ACATTGAGTT TTACTTTGTG GAAGAGAATT AGATTCTCGT GTTAGTAAAA
 601 TCGGTTAGTA ATTGATGATG CATTATTTTT ACTCTATAAT AGAGATGCAA
 651 TTTTATTTTT GCATTTGGG ATCAAATTGT AATGCAGTCA TATATTGATT
 701 TCATAAATGT TTGGGATATT GTTGGTTATT TAACTAGAAA TAGACTTCTT
 751 ATTTCATATT TATTGTTAAA ATCCTTTATT GGAGATGAAT TATTTGTTCA
 801 CCGATTAGAA GTTGATAGTC GCTTTTGTTT TAGAAGAAAT TTTACCGTAG
 851 ACCAAGTTAA GGAGTTTTAG AAGCACTTTG CATGGGAGCA TTAGTGTATG
 901 TTATGGCTTT ATCAAATATA GGTTTTGAAG ATTCAGAGAG CCAAGAAAAG
 951 CTAGAACCCA AGAACTAGGA AGTTAGAGTA ATTCACAATA CCATAACGTG
1001 ATATAAAACT TTTTATTGTA ACTCAAATCG GTAATATTTT TTGCTTTAGT
1051 CTTAATCGAT AAATTATTTT TTTATATTGA TTAGTTATAG GAGGCTCACA
1101 AAGTTGGGAA TAATTAAAAT ATCATATTTT GTATTTGAAC AATTTATGAA
1151 ATAGTAATTG GTAAAAAATC ACTTTAAATT TTTATCCTAT ATCCAGAAGG
1201 ATTATGGTGT CTGGCATAGT TGTTTGGAAG ATTTGAATCA GGGTAAAAGT
1251 ATGTTGTAAT TTTTATTTTG TTATAGGCAT TTTTTGTGCT TGATTGTTTT
1301 GTTGTCATTA TATTTTATTA TTTGGAAGTG TATATATATG TTTGATTAAA
1351 ATATAGATAA TCAATTTTAT AAGAAATTTG CAACAATTAC ACAAGGATAA
1401 AGTCTACAAT ATGCGAGTAA AATTTGATTG AACCTAGGAT GTCATATTTA
1451 ATGCATATTT TATTTCAATG TGTTTATTAT ACATCTATTG TATTATATG
```

FIG. 3. (continued)

| CLONE | %AT | BINDING STRENGTH | GRAPHIC REPRESENTATION |
|---|---|---|---|
| pS116-1 (SEQ ID NO: 5) | 76.6 | 90 | |
| RB7-6 (SEQ ID NO: 20) | 73.2 | 80 | |
| pS211-1 (SEQ ID NO: 10) | 71.7 | 70 | |
| pS220-1 (SEQ ID NO: 13) | 73.1 | 70 | |
| pS226-1 (SEQ ID NO: 9) | 77.1 | 60 | |
| pS205-2 (SEQ ID NO: 8) | 71.4 | 50 | |
| Ps217-1 (SEQ ID NO: 11) | 65.2 | 40 | |

FIG. 4.

| CLONE | %A+T | BINDING STRENGTH | GRAPHIC REPRESENTATION |
|---|---|---|---|
| pS202-1 (SEQ ID NO: 6) | 68.3 | 40 | |
| pS202-2 (SEQ ID NO: 7) | 64.9 | 40 | |
| pS115 (SEQ ID NO: 4) | 65.7 | 40 | |
| pS4 (SEQ ID NO: 2) | 72.2 | 20 | |
| pS1 (SEQ ID NO: 1) | 71.8 | 20 | |
| pS8 (SEQ ID NO: 3) | 61.6 | 0 | |
| pS218 (SEQ ID NO: 12) | 62.0 | 0 | |

FIG. 4A.

MATRIX ATTACHMENT REGIONS

This application claims the benefit of U.S. Provisional Application No. 60/066,118, filed Aug. 6, 1997.

This invention was made with Government support under National Science Foundation Award MCB-9418491 and USDA Grant 91-37301-6377. The Government may have certain rights to this invention.

FIELD OF THE INVENTION

The present invention relates to matrix attachment regions isolated from a higher plant, and to methods for isolating matrix attachment sequences.

BACKGROUND OF THE INVENTION

The proteinaceous nuclear 'matrix' or 'scaffold' in the cell nucleus plays a role in determining chromatin structure. Electron micrographs show that nuclear DNA is attached to this scaffold at intervals to produce a series of loops (Zlatanova and Van Holde, *J. Cell Sci.* 103:889 (1992)). Matrix Attachment Regions (MARs; also referred to a scaffold attachment regions or SARs) are genomic DNA sequences which bind specifically to components of the nuclear matrix. See Boulikas, *J. Cell. Biochem.* 52:14 (1993). These sequences are thought to define independent chromatin domains through their attachment to the nuclear matrix. Both transcription and replication are thought to occur at the nuclear matrix.

Transformation of a cell using a; transgene flanked by one or more MARs has been shown to increase expression of the transgene product, compared to transformation using a construct lacking MARs. See Allen et al., *Plant Cell* 8:899 (1996); Bonifer et al., *EMBO J.* 9:2843 (1990); McKnight et al., *Proc. Natl. Acad. Sci. USA* 89:6943 (1992); Phi-Van et al., *Mol. Cell. Biol.* 10:2303 (1990)). Flanking a GUS reporter gene with yeast MARs has been reported to result in higher and less variable transgene expression in plant cells. Allen et al. *Plant Cell* 5:603 (1993).

SUMMARY OF THE INVENTION

In view of the foregoing, a first aspect of the present invention is an isolated DNA molecule having a nucleotide sequence selected from the group consisting of SEQ ID NOS:1, 2, 4–11 and 13, sequences that hybridize to this isolated DNA under stringent conditions.

A further aspect of the present invention is a DNA construct comprising a transcription initiation region, a structural gene operatively associated with the transcription initiation region, and at least one matrix attachment region of the present invention positioned either 5' to the transcription initiation region or 3' to the structural gene.

A further aspect of the present invention is a vector comprising a DNA construct as described above, including plasmids, viruses and plant transformation.

A further aspect of the present invention is a host cell containing a DNA construct as described above, including plant and animal host cells.

A further aspect of the present invention is a method of identifying matrix attachment regions in a DNA molecule of known nucleotide sequence, by identifying a sequence section of at least twenty contiguous nucleotides that is at least 90% A or T nucleotides. The method may further comprise preparing a MAR molecule of at least about 300 nucleotides, comprising the identified MAR motif.

BRIEF DESCRIPTION OF THE INVENTION

FIGS. 1A–F provide maps depicting generalized plasmids from the cloning of random matrix associated DNA into pBluescript II SK+. 1A is DNA isolated after digestion with RsaI and ligated into the EcoRV site (clones 1–4, 6–8, 2–23 and 26–28). 1B is DNA isolated after digestion with EcoRI and ligated into the EcoRI site (clones 11, 15, 34 and 35). 1C is DNA isolated after digestion with EcoRI and ligated into the EcoRI site (clones 109, 113, 115 and 116). ID is DNA isolated after digestion with HindIII and ligated into the HindIII site (clones 201–203, 205, 206, 209, 211 and 216–220). 1E is DNA isolated after digestion with DnaseI and ligated into the HincII site (clones 302, 203, 205, 311 and 319). 1F is a map of ToRB7-6 which serves as a positive control in the exogenous binding assay.

Figure 2W:
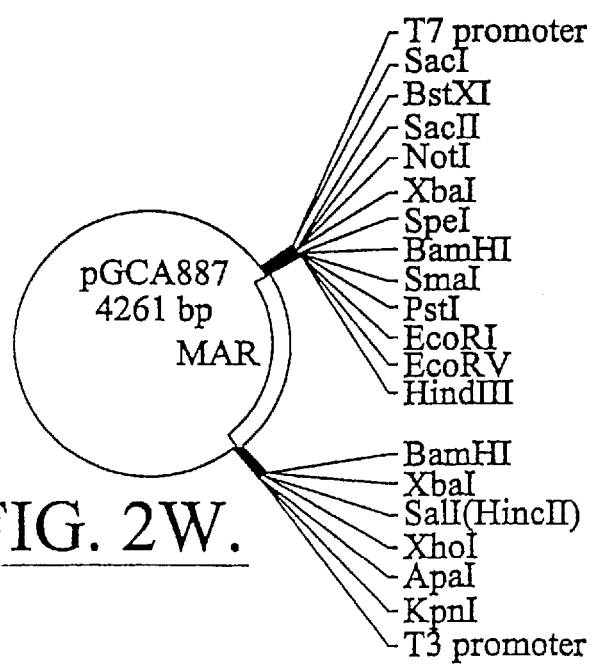

FIGS. 2A–W provide plasmid maps of specific clones or subclones chosen for sequencing. Inserts are indicated by shaded boxes labeled either 'MAR' for binding clones or 'insert' for non-binding clones. 2A is plasmid pS1 containing MAR SEQ ID NO:1; 2B is plasmid pS4 containing MAR SEQ ID NO:2; 2C is plasmid pS8 containing non-binding SEQ ID NO:3; 2D is plasmid pS115 containing MAR SEQ ID NO:4; 2E is MAR plasmid pS116; 2F is plasmid pS 116-1.1 containing MAR SEQ ID NO:5, which is a smaller core binding fragment of clone 116; 2G is MAR plasmid pS202; 2H is plasmid pS202-1 containing MAR SEQ ID NO:6, which is one of two binding fragments of clone 202; 2I is plasmid pS202-2 containing MAR SEQ ID NO:7, which is the second of two binding fragments of clone 202; 2J is plasmid pS203 containing a non-binding insert; 2K is MAR plasmid pS205; 2L is plasmid pS205-2 containing MAR SEQ ID NO:8; which is a core binding sequence from clone 205; 2M is MAR plasmid pS206; 2N is plasmid pS206-1 containing MAR SEQ ID NO:9, which is a core binding sequence from clone 206; 2O is MAR plasmid pS211; 2P is plasmid pS211-1 containing MAR SEQ ID NO:10, which is a core binding sequence from clone 211; 2Q is MAR plasmid pS217; 2R is plasmid pS217-1 containing MAR SEQ ID NO:11, which is a core binding sequence from clone 217; 2S is plasmid pS218 containing non-binding insert SEQ ID NO:12; 2T is MAR plasmid pS220; 2U is plasmid pS220-1 containing MAR SEQ ID NO:13, which is a core binding sequence from clone 220; 2V is plasmid pRB7-6, containing the MAR ToRB7-6 fragment (SEQ ID NO:20) used as a positive control); 2W is plasmid pGCA887 (containing an insert from yeast ARS1 cloned into the vector pBCKS+(Stratogene)), which serves as a standard for weak binding to the nuclear matrix (SEQ ID NO:21).

FIG. 3 provides the sequences of the MAR clones and subclones of the present invention, and the control sequences of the known TobRB7 MAR (SEQ ID NO:20) and yeast ARS1 MAR (SEQ ID NO:21).

FIG. 4 provides graphic representations depicting the locations of different MAR DNA motifs within the sequenced clones or subclones. Binding strengths are indicated on a scale of 0–100. The A box (AATAAAYAAA) (SEQ ID NO:14) is represented by "A", with 8/10 matches required for motif identification. The T box (TTWTWTTWTT) (SEQ ID NO:15) is represented by "T", with 9/10 matches required for motif identification. The ARS consensus sequence (WTTTATRTTTW) (SEQ ID NO:16) is represented by 'R', with 10/11 matches required for motif identification. The topoisomerase II consensus sequence (GTNWAYATTNATNNR) (SEQ ID NO:17) is represented by 'O', with 13/15 matches required for motif identification. If motifs overlapped, only one is shown. Filled boxes indicate stretches of 20 base pairs consisting of ≧90% AT DNA. Base unwinding regions are represented by 'U' (AATATATTT; SEQ ID NO:22; Bode et al., *Science* 255:195 (1992)).

Figure 5:
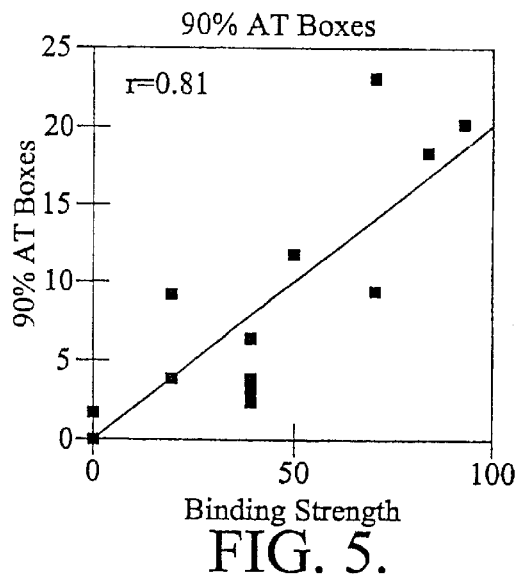

FIG. 5 graphs the numbers of blocks of 20 or more nucleotides that consist of 90% or greater A or T nucleotides found in the sequenced clones (SEQ ID NOS:1, 2, 4–11 and 13) versus binding strength (indicated as between 0–100). The two well-characterized MARs (TobRB7 and ARS1), as well as two non-binding clones (SEQ ID NOS:3 and 12) were included in the analysis.

Figure 6:
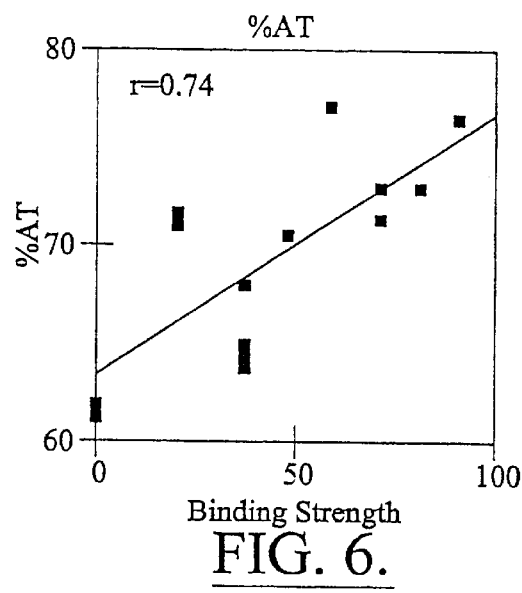
Figure 7:
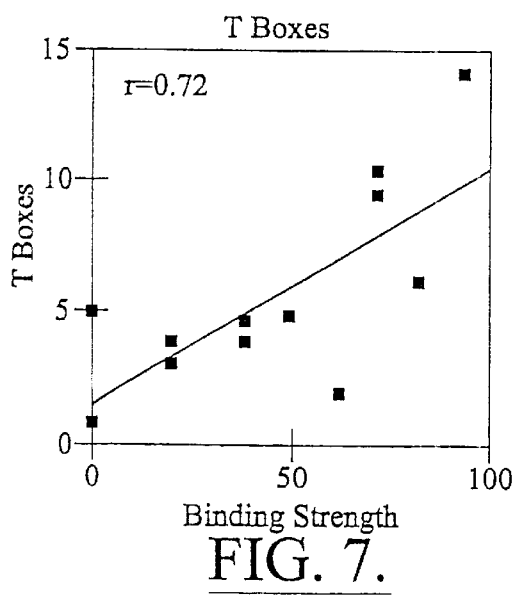

FIG. 6 graphs the % AT found in the sequenced clones (SEQ ID NOS:1, 2, 4–11 and 13) versus binding strength (indicated as between 0–100). The two well-characterized MARs (TobRB7 and ARS1), as well as two non-binding clones (SEQ ID NOS:3 and 12) were included in the analysis FIG. 7 graphs the number of T boxes found in the sequenced clones (SEQ ID NOS:1, 2, 4–11 and 13) versus binding strength (indicated as between 0–100). The two well-characterized MARs (TobRB7 and ARS1), as well as two non-binding clones (SEQ ID NOS:3 and 12) were included in the analysis.

Figure 8:
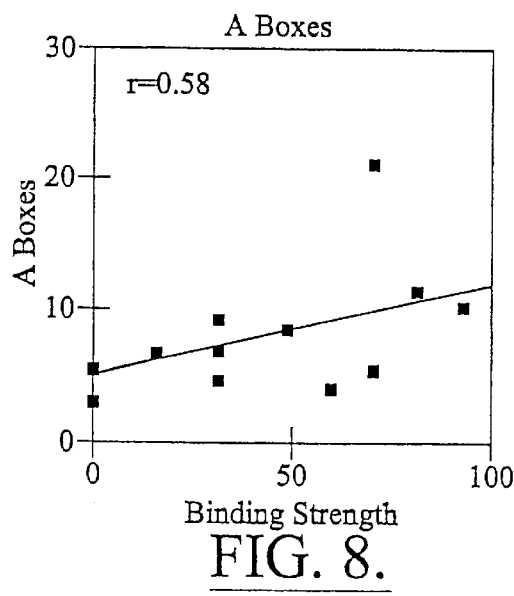

FIG. 8 graphs the number of A boxes found in the sequenced clones (SEQ ID NOS:1, 2, 4–11 and 13) versus binding strength (indicated as between 0–100). The two well-characterized MARs (TobRB7 and ARS1), as well as two non-binding clones (SEQ ID NOS:3 and 12) were included in the analysis.

Figure 9:
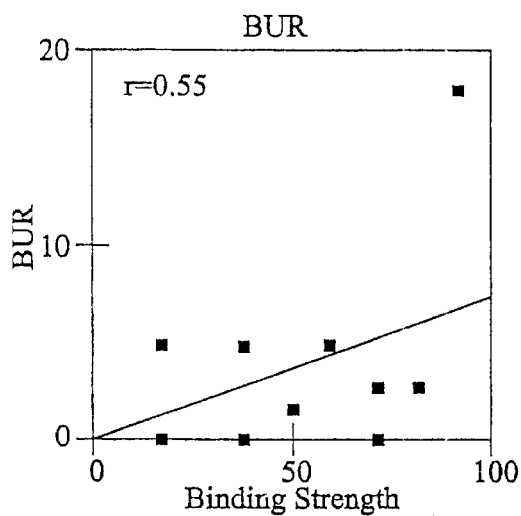

FIG. 9 graphs the number of base unwinding regions (BUR; SEQ ID NO:22) found in the sequence clones (SEQ ID NOS:1, 2, 4–11 and 13) versus binding strength (indicated as between 0–100). The two well-characterized MARs (TobRB7 and ARS1), as well as two non-binding clones (SEQ ID NOS:3 and 12) were included in the analysis.

Figure 10:
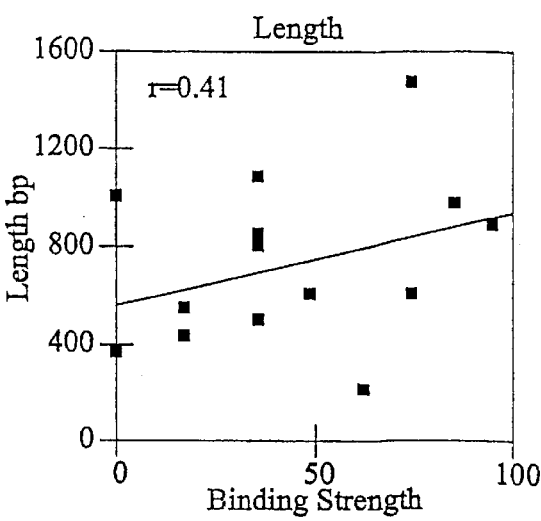

FIG. 10 graphs the length of the sequenced clones (SEQ ID NOS: 1, 2, 4–11 and 13) versus binding strength (indicated as between 0–100). The two well-characterized MARs (TobRB7 and ARS1), as well as two non-binding clones (SEQ ID NOS:3 and 12) were included in the analysis.

Figure 11:
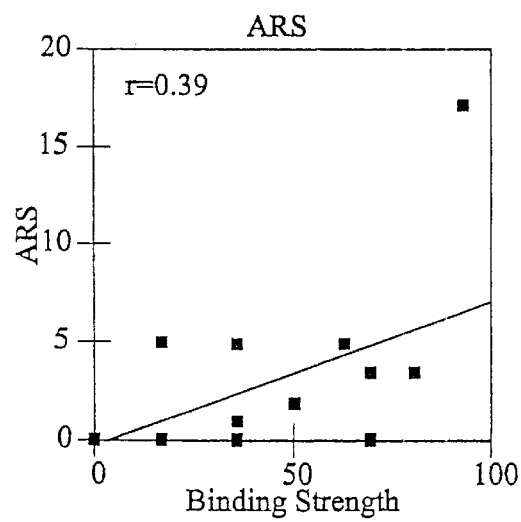

FIG. 11 graphs the number of ARS motifs found in the sequenced clones (SEQ ID NOS:1, 2, 4–11 and 13) versus binding strength (indicated as between 0–100). The two well-characterized MARs (TobRB7 and ARS1), as well as two non-binding clones (SEQ ID NOS:3 and 12) were included in the analysis.

Figure 12:
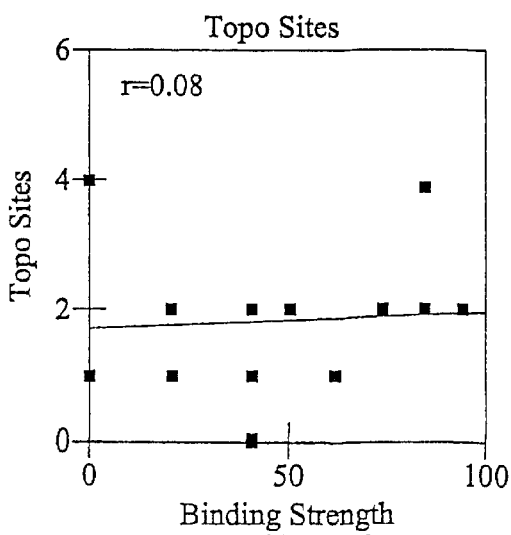

FIG. 12 graphs the number of Topoisomerase motifs found in the sequenced clones (SEQ ID NOS:1, 2, 4–11 and 13) versus binding strength (indicated as between 0–100). The two well-characterized MARs (TobRB7 and ARS1), as well as two non-binding clones (SEQ ID NOS:3 and 12) were included in the analysis.

DETAILED DESCRIPTION OF THE INVENTION

Matrix attachment regions (MARs) are structural components of chromatin that form topologically constrained loops of DNA through their interaction with the proteinaceous nuclear matrix. MARs have been found to co-localize with a variety of functional elements within the nucleus including transcriptional domain boundaries (Jarman and Higgs, EMBO J. 7:3337 (1988); Phi Van and Sträitling, EMBO J. 7:655 (1988); Levy-Wilson and Fortier, J. Biol. Chem. 264:21196 (1990)), promoters, enhancers (Gasser and Laemmli, Cell 46:521 (1986); Cockerill and Garrard, Cell 44:273 (1986); van der Geest, Plant J. 6:413 (1994)), introns (Kas and Chasin, J. Mol. Biol. 194:677 (1987); Forrester et al., Science 265:1221 (1994)) and putative origins of replication (Brylawski et al., Cancer Res. 53:3865 (1993)), suggesting that MARs may play functional roles in addition to their purely structural role within the nucleus. It appears that not all MARs are involved in the same processes, and that categories or groups of these elements with distinct features and functions exist.

The characteristics of MARs that dictate their binding to the nuclear matrix are not known. Presently, the only definition of a MAR is operational, based on the ability to bind to the nuclear matrix. It is known that MARs are AT rich, but not all AT-rich DNA will bind to the nuclear matrix. MARs have also been reported to contain a number of short sequence motifs, but the necessity of these motifs has not been established. Motifs reported to occur in MARs include A boxes, T boxes, the ARS consensus and the consensus sequence for Drosophila topoisomerase. In addition, several secondary structure motifs have been reported to be associated with MARs including base pair unwinding regions, bent DNA and single stranded regions.

To date most matrix attachment regions have been identified through their association with a well-characterized gene. This type of sampling creates a bias that could hinder efforts in defining MAR sequences. It would be useful to be able to identify MARs by sequence alone. The present inventors obtained a group of DNA fragments that were MARs by operational definition, by purifying DNA associated with tobacco NT-1 nuclear matrices prepared using several different nucleases. These sequences were cloned and tested for their ability to rebind to the nuclear matrix, in order to identify MARs. Once MARs were identified, they were sequenced and analyzed for AT content and the presence of common motifs. The significance of each identified motif was assessed through correlation with the binding strength of MARs to the nuclear matrix.

The present inventors identified a number of novel MAR sequences, and identified a new MAR motif whose frequency significantly correlates with the binding strength of a MAR. The present inventors found no significant correlation between binding strength and the length of the MAR fragment. However, a significant relationship between binding strength and overall AT content was identified. This is the first report of a correlation between the abundance of certain MAR related motifs and MAR binding strength. In addition, the newly identified MAR related motif of local AT rich regions (sections of 20 contiguous nucleotides that are ≧90% A and/or T), has a higher correlation to MAR binding strength than any of the previously identified motifs. These findings provide a method for the identification of MAR regions in DNA molecules of known nucleotide sequence. The method comprises identifying, in the known DNA sequence, regions or areas of the sequence which are at least 20 contiguous nucleotides in length and which consist of at least 90% A and/or T nucleotides. The presence of a 20-bp region of ≧90% AT indicates a MAR; a MAR may contain multiple regions of ≧90% AT. The identification of such regions may be carried out by techniques that are well-known in the art, including sequencing the DNA to be screened and reviewing a printed DNA sequence for such regions. Contiguous fragments of the original DNA sequence that are from one to several kilobases (from about 3,000 nucleotides, 2,000 nucleotides, or about 1,000 nucleotides) in length to about 500, 400, or 300 bases in length, and which encompass the 20-bp regions of ≧90% AT can then be isolated (or created de novo by known synthesis techniques) and utilized as MARs. Optionally, the isolated fragments can first be tested for MAR binding strength, for example using an exogenous nuclear matrix binding assay as described herein.

The identification of such regions may be carried out be techniques that are well-known in the art, including sequencing the DNA to be screened and reviewing the printed DNA sequence for such regions. Fragments of the original DNA sequence that are from several kilobases in length to about 500, 400, or 300 bases in length, and which encompass the 20-bp regions of ≧90% AT can then be isolated (or created de novo by known synthesis techniques) and utilized as MARS. Optionally, the isolated fragments can first be tested for MAR binding strength, for example using an exogenous nuclear matrix binding assay as described herein.

MARs in nature are double-stranded genomic DNA molecules. The MARs of the present invention include those of SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:13. The sequences provided represent one strand of the double-stranded MAR DNA; the sequence of the complementary strand is readily apparent to those of ordinary skill in the art.

It will be apparent to those of skill in the art that minor sequence variations from the sequences provided above will not affect the function of the MARs of the present invention. MAR DNA sequences of the present invention include sequences that are functional MARs which hybridize to DNA sequences of SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:13 (or the complementary sequences thereto) under stringent conditions. For example, hybridization of such sequences may be carried out under conditions represented by a wash stringency of 0.3M NaCl, 0.03M sodium citrate, and 0.1% SDS at 60° C., or even 70° C., in a standard in situ hybridization assay. (See J. Sambrook et al., Molecular Cloning, A Laboratory Manual (2d ed. 1989)(Cold Spring Harbor Laboratory)). In general, DNA sequences that act as MARs and hybridize to the DNA sequences give above will have at least 70%, 75%, 80%, 85%, 90%, 95% or even 97% or greater sequence similarity to the MAR sequences provided herein. (Determinations of sequence similarity are made with the two sequences aligned for maximum matching; gaps in either of the two sequences being matched are allowed in maximizing matching.)

MARs of the present invention may consist of or comprise the specific sequences provided herein, or nucleotide sequences having substantial sequence similarity to the sequences provided herein that retain MAR functions. As used herein, 'substantial sequence similarity' means that DNA which have slight and non-consequential sequence variations from the specific sequences disclosed herein are considered to be equivalent to the disclosed sequences. In this regard, 'slight and non-consequential' sequence variations mean that sequences with substantial sequence similarity will be functionally equivalent to the sequences disclosed and claimed herein. Functionally equivalent sequences will function in substantially the same manner as the sequences disclosed and claimed herein.

DNA constructs of the present invention may be used to transform cells from a variety of organisms, including animal and plants (i.e., vascular plants). As used herein, plants includes both gymnosperms and angiosperms (i.e., monocots and dicots). As used herein, animals includes mammals, both primate and non-primate. Transformation according to the present invention may be used to increase expression levels of transgenes in stably transformed cells. Cells may be transformed while in cell culture; while in vivo or in situ in a tissue, organ, or intact organism.

The term "operatively associated," as used herein, refers to DNA sequences on a single DNA molecule which are associated so that the function of one is affected by the other. Thus, a transcription initiation region is operatively associated with a structural gene when it is capable of affecting the expression of that structural gene (i.e., the structural gene is under the transcriptional control of the transcription initiation region). The transcription initiation region is said to be "upstream" from the structural gene, which is in turn said to be "downstream" from the transcription initiation region.

DNA constructs, or "expression cassettes," of the present invention preferably include, 5' to 3' in the direction of transcription, a first matrix attachment region, a transcription initiation region, a structural gene operatively associated with the transcription initiation region, a termination sequence including a stop signal for RNA polymerase and a polyadenylation signal for polyadenylation (e.g., the nos terminator), and a second matrix attachment region. All of these regions should be capable of operating in the cells to be transformed. The termination region may be derived from the same gene as the transcription initiation or promoter region, or may be derived from a different gene.

The matrix attachment regions (or "MARs") of the present invention have a nucleotide sequence selected from the group consisting of SEQ ID NOS:1, 2 4–11 and 13 provided herein. These MARs may be isolated from natural sources or may be chemically synthesized.

MARs are known to act in an orientation-independent manner. Poljak et al., *Nucleic Acids Res.* 22:4386 (1994). Genetic constructs of the present invention may contain MARs oriented in either direction (5'-3' or 3'-5'), as direct repeats in a single orientation (→→), direct repeats in the opposite orientation (←←), or either of two possible indirect repeats (←→) or (→←). The genetic constructs of the present invention may contain a single MAR as disclosed herein, multiple MARs of the present invention, or MARs of the present invention in conjunction with other MARs. A DNA construct of the present invention may comprise a first MAR of the present invention 5' to the transcription initiation region and a second MAR of a different sequence situated 3' to the structural gene, or vice versa.

The transcription initiation region, which preferably includes the RNA polymerase binding site (promoter), may be native to the host organism to be transformed or may be derived from an alternative source, where the region is functional in the host. Other sources include the Agrobacterium T-DNA genes, such as the transcriptional initiation regions for the biosynthesis of nopaline, octapine, mannopine, or other opine transcriptional initiation regions, transcriptional initiation regions from plants, transcriptional initiation regions from viruses (including host specific viruses), or partially or wholly synthetic transcription initiation regions. Transcriptional initiation and termination regions are well known. See, e.g., dGreve, *J. Mol. Appl. Genet.* 1, 499–511 (1983); Salomon et al., *EMBO J.* 3, 141–146 (1984); Garfinkel et al., *Cell* 27, 143–153 (1983); and Barker et al., *Plant Mol. Biol.* 2, 235–350 (1983).

The transcriptional initiation regions may, in addition to the RNA polymerase binding site, include regions which regulate transcription, where the regulation involves, for example, chemical or physical repression or induction (e.g., regulation based on metabolites or light) or regulation based on cell differentiation (such as associated with leaves, roots, seed, or the like in plants). Thus, the transcriptional initiation region, or the regulatory portion of such region, is obtained from an appropriate gene which is so regulated. For example, the 1,5-ribulose biphosphate carboxylase gene is light-induced and may be used for transcriptional initiation. Other genes are known which are induced by stress, temperature, wounding, pathogen effects, etc.

Structural genes are those portions of genes which comprise a DNA segment coding for a protein, polypeptide, or portion thereof, possibly including a ribosome binding site and/or a translational start codon, but lacking a transcription initiation region. The term can also refer to introduced copies of a structural gene where that gene is also naturally found within the cell being transformed. The structural gene may encode a protein not normally found in the cell in which the gene is introduced or in combination with the transcription initiation region to which it is operationally associated, in which case it is termed a heterologous structural gene. Genes which may be operationally associated with a transcription initiation region of the present invention for expression in a plant species may be derived from a chromosomal gene, cDNA, a synthetic gene, or combinations thereof. Any structural gene may be employed. Where plant cells are transformed, the structural gene may encode an enzyme to introduce a desired trait, such as glyphosphate resistance; a protein such as a *Bacillus thuringiensis* protein (or fragment thereof) to impart insect resistance; or a plant virus protein or fragment thereof to impart virus resistance.

The expression cassette may be provided in a DNA construct which also has at least one replication system. For convenience, it is common to have a replication system functional in *Eschenichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly a plant host. The markers may be protection against a biocide, such as antibiotics, toxins, heavy metals, or the like; provide complementation, for example by imparting prototrophy to an auxotrophic host; or provide a visible phenotype through the production of a novel compound. Exemplary genes which may be employed include neomycin phosphotransferase (NPTII), hygromycin phosphotransferase (HPT), chloramphenicol acetyltransferase (CAT), nitrilase, and the gentarnicin resistance gene. For plant host selection, non-limiting examples of suitable markers are β-glucuronidase, providing indigo production, luciferase, providing visible light production, NPTII, providing kanamycin resistance or G418 resistance, HPT, providing hygromycin resistance, and the mutated aroA gene, providing glyphosate resistance.

The various fragments comprising the various constructs, expression cassettes, markers, and the like may be introduced consecutively by restriction enzyme cleavage of an appropriate replication system, and insertion of the particular C construct or fragment into the available site. After ligation and cloning the DNA construct may be isolated for further manipulation. All of these techniques are amply exemplified in the literature and find particular exemplification in Sambrook et al., Molecular Cloning: A Laboratory Manual, (2d Ed. 1989)(Cold Spring Harbor Laboratory, Cold Spring Harbor, N.Y).

Vectors which may be used to transform plant tissue with DNA constructs of the present invention include vectors used for Agrobacterium-mediated transformation and ballistic vectors, as well as vectors suitable for direct -DNA-mediated transformation.

Microparticles carrying a DNA construct of the present invention, which microparticles are suitable for the ballistic transformation of a cell, are also useful for transforming cells according to the present invention. The microparticle is propelled into a cell to produce a transformed cell. Where the transformed cell is a plant cell, a plant may be regenerated from the transformed cell according to techniques known in the art. Any suitable ballistic cell transformation methodology and apparatus can be used in practicing the present invention. Exemplary apparatus and procedures are disclosed in Stomp et al., U.S. Pat. No. 5,122,466; and Sanford and Wolf, U.S. Pat. No. 4,945,050 (the disclosures of all U.S. Patent references cited herein are incorporated herein by reference in their entirety). When using ballistic transformation procedures, the expression cassette may be incorporated into a plasmid capable of replicating in the cell to be transformed. Examples of microparticles suitable for use in such systems include 1 to 5 μm gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristeinmatic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. A dominant selectable marker (such as npt II) can be associated with the expression cassette to assist in breeding.

Plants which may be employed in practicing the present invention include (but are not limited to) tobacco (*Nicotiana tabacum*), potato (*Solanum tuberosum*), soybean (*glycine max*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadania integnfolia*), almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), lettuce (e.g., *Lactuea sativa*), green beans (*Phaseolus vulgaris*), lima beans (*Phaseolus limensis*), peas (Pisum spp.) and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*dianthus caryophyllus*), poinsettia (*Euphorbia pulcherima*), and chrysanthemum. Gymnosperms which may be employed to carrying out the present invention include conifers, including pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The examples which follow are set forth to illustrate the present invention, and are not to be construed as limiting thereof.

EXAMPLE 1

Materials and Methods

NT-1 Protoplast Isolation

One hundred ml cultures of four day old tobacco NT-1 suspension cells were spun at 1400 rpm (585×g) for five minutes in a Beckman GPR table top centrifuge rotor GH 3.7 and washed in 10 mM MES (2-[N-morpholino]ethanesulfonic acid sodium salt, Sigma M-3885) pH 5.5, 0.4M mannitol. The pellet was resuspended in 100 ml of 10 mM MES pH 5.5, 0.4M mannitol containing 1 g of cellulase (Onozuka RS Yakult Pharmaceutical LTD) and 0.1 g of pectolyase (Y-23 Seishin Corp.) and incubated for 30 to 60 minutes at 28° C. with gentle shaking in order to remove the cell wall. The resulting protoplasts were pelleted at 1400 rpm and washed two times in 50 ml of cold (4° C.) 0.4 mannitol (unbuffered).

NT-1 Nuclei Isolation

The protoplasts were pelleted and resuspended in 50 ml of Nuclei Isolation Buffer 1 (NIB1) at pH 6.5 (NIB1=0.5M hexylene glycol, 20 mM N-2-hydroxyethylpiperazine-N-ethanesulfonic acid (hepes), 20 mM KCl, 1% thiodiglycol, 50 mM spermine (Sigma S-2876), 125 mM spermidine (Sigma S-2501), 0.5 mM phenylmethylsulfonyl fluoride (PMSF 2M stock in methanol), 2 µg/ml aprotinin (Sigma A-6279), 0.5% Triton X-100, 0.5 mM EDTA). This procedure solubilizes the plasma membrane and releases nuclei. After a five minute incubation on ice, the nuclei were filtered through a tier of 100 um, 50 um, and 30 um nylon mesh to remove the cellular debris and then spun through 15% Percoll (Pharmacia 17-0891-01)/NIB1 for further purification. The pelleted nuclei were washed two times with of Nuclei Isolation Buffer 2 (NIB2=NIB 1 without EDTA).

Quantification of Nuclei

The nuclei were resuspended in a suitable volume of storage buffer (NIB2 in 50% glycerol) such that the suspension would have an absorbance reading of 10 at 260 nm. Absorbance was determined by diluting 2 µl of nuclei in 0.5 ml of 2.2M sodium chloride, 5.5M urea. One ml aliquots were stored at −70° C. until needed. The number of nuclei per tube was determined by counting aliquots using a hemocytometer. Although there was some variation between preparations, in general, each 1 ml tube with an absorbance of 10 contains about 3.5 million nuclei.

Preparation of Nuclear Halos and Nuclear Matrices

Approximately 3.5 million nuclei (one tube stored at −70° C.) were thawed on ice and washed in 10 ml of Nuclei Isolation Buffer 3 (NIB3=0.5M hexylene glycol, 20 mM hepes pH 7.4, 20 mM KCl, 1% thiodiglycol, 50 mM spermine, 125 mM spermidine, 0.5 mM PMSF, 2 µg/ml aprotinin). The nuclei were pelleted at 1400 rpm, resuspended in 200 µl of NIB3 containing 1 mM $CuSO_4$ and incubated at 42° C. for 15 minutes in order to stabilize the nuclear matrix.

To remove the histones and other soluble proteins, the nuclei were incubated in 10 ml of Halo Isolation Buffer 2 (HIB2=10 mM 3,5 duiodosalicylic acid lithium salt (Sigma D-3635), 100 mM lithium acetate, 20 mM hepes, 2 mM EDTA, 0.1% digitonin, 0.5 mM PMSF, 2 µg/ml aprotinin) for 15 minutes at room temperature. (Digitonin is prepared by mixing 5 g in 12.5 ml of methanol, heating to 65° C. to dissolve, filtering through Whatmnan #1 filter paper, recrystalizing by removing the methanol under vacuum, weighing the resulting crystals and resuspending in water at a concentration of 5%, and storing at −20° C. until needed). When histones are removed the coiling restraints on the DNA are removed, allowing the DNA to spill out of the nucleus to form a 'nuclear halo'.

The nuclear halos were pelleted at 3600 rpm (2900×g) and then washed with 10 ml of Digestion/Binding Buffer (D/BB=70 mM NaCl, 20 mM Tris-HCl pH 8.0, 20 mM KCl, 0. 1% digitonin, 1% thiodiglycol, 50 mM spermine, 125 mM spermidine, 2 µg/ml aprotinin and 0.5 mM PMSP). The second wash contained all the elements of the first wash, plus 10 uM phenanthroline, and the third wash contained all the elements of the second was plus 10 mM $MgCl_2$. The halos were resuspended in 500 µl of D/BB plus all the elements of wash three.

For a discussion of the above-described methods, see Hall and Spiker, *Plant Molecular Biology Manual* D2: 1–12, Kluwer Academic Publishers, Dordrecht, the Netherlands.

To cleave the DNA, nuclear halos were treated with nucleases (either 250 U of RsaI, TaqI, EcoRI, HindIII, or with DnaseI (Sigma) at 0.1 µg/ml) and incubated at 37° C. for 90 minutes with the addition of another 250 U of restriction enzymes or 0.1 µg/ml of DnaseI after 45 minutes. The resulting nuclear matrices and their associated DNA were separated from unbound DNA by centrifugation at 3600 rpm for 5 minutes.

Isolation of functionally-defined MAR DNA

Nuclear matrices were washed with 1 ml of D/BB and 10 mM $MgCl_2$ to remove residual supernatant (unbound) DNA and to remove protease inhibitors. The pellet was resuspended in 500 µl of protease buffer (10 nM Tris-HCl pH 8.0, 20 mM EDTA, 0.5% SDS, 0.5 mg/ml proteinase K) and incubated at room temperature overnight. The matrix bound DNA was further purified by phenol:chloroform extraction and ethanol precipitation, dried and resuspended in 100 μl of Tris-EDTA (TE=10 nM Tris-HCl pH8.0 and 10 mM EDTA).

Cloning

The purified operationally defined MAR DNA fragments were cloned into pBluescript II SK+(Stratagene). The vector was digested with either EcoRV, ClaI, EcoRI, Hind III or HincII (for blunt end ligation of DnaseI generated fragments), and ligated (using New England Biolabs T4 ligase according to the manufacturer's protocol) to the purified DNA from the nuclear matrices purified with RsaI, TaqI, EcoRI, HindIII, or DnaseI. Stratagene *E. coli* SURE cells were transformed with the plasmids according to the manufacturer's protocol.

Isolation of Plasmid DNA

Plasmid DNA was isolated from transformants that were grown in 2 ml of Luria Broth (10 g/l tryptone, 10 g/l yeast extract, 5 g/l NaCl) with 80 μg/ml ampicillin overnight at 37° C. with shaking. The cells were spun at 13000 rpm in a microfuge for 2 minutes, and the pellets were resuspended in 150 μl of 20% sucrose, 25 mM Tris-HCl pH 8.0, 10 mM EDTA. The cells were treated with 350 μl of lysis buffer (1% SDS and 200 mM NaOH) and incubated at room temperature for 10 minutes. After the addition of 250 μl of 3M sodium acetate pH 5.2, the cells were incubated on ice for 10 minutes and then spun at 13000 rpm for 20 minutes at 4° C. The plasmid-DNA containing supernatant was transferred to a fresh tube containing 0.7 ml of isopropanol and spun at 13000 rpm for 20 minutes at 4° C. The pellets were washed with 70% ethanol, air dried overnight and then resuspended in 50 μl of TE containing 5 μg of Rnase A (Sigma), incubated at 37° C. for 1 hour and stored at 4° C. until needed. Alternatively, when large quantities of DNA were required, plasmid DNA was isolated using Qiagen columns according to the manufacturer's protocol.

End Labeling Protocol

Plasmid DNAs isolated from individual transformants were end labeled and tested for binding to the nuclear matrix. One μg of plasmid DNA was digested with the appropriate enzymes to release the fragment (usually EcoRI and HindIII) according to the manufacturer's protocol. A standard end-labeling reaction contained 250 ng of digested DNA (5 μl), 0.5 μl of 10 X Klenow buffer, 0.33 μl of dNTPs (2 mM deoxycytosine triphosphate, 2 mM deoxyguanidine triphosphate and 2 mM deoxythymidine triphosphate), 2.5 μl of 10 mCi/ml α-$^{32}$P deoxyadenosine triphosphate (Dupont NEN BLU-012H) and 0.2 μl of 5,000 U/ml DNA polymerase large fragment (NEB Klenow) in a total of 10 μl. The mixture was incubated at room temperature for 15 minutes and the reaction stopped by the addition of 40 μl of TE. The unincorporated nucleotides were removed by centrifugation through a Sephadex G-50 spin column. The amount of radioactivity (counts per minute) in the resulting end-labeled DNA was determined by placing 2 μl of labeled DNA in 3 ml of Scinti Verse (Fisher SX 1–4) and counted using the Beckman LS 100C scintillation counter.

Matrix Binding-Exogenous Assay

Nuclear halos were treated with 250 U of EcoRI and HindIII for 90 minutes at 37° C. with the addition of another 250 U of each enzyme after 45 minutes. The resulting nuclear matrices were aliquoted at 50 μl for different binding reactions (different labeled DNA fragments for testing). Each 50 μl aliquot contained one tenth of the nuclear matrices, about 350,000, as well as one tenth of the cleaved, non-MAR, endogenous DNA, which served as nonspecific competitor. Radioactively labeled DNA fragments of interest were incubated with the nuclear matrices at 50,000 cpm per fragment (about 5 ng of DNA) per 50 μl reaction at 37° C. for 3 hours with resuspension every 20 minutes. The pellet and supernatant fractions were separated by centrifugation at 3600 rpm for 5 minutes. The supernatant was transferred to a fresh tube containing 0.5 μl of 0.5M EDTA pH 8.0 and stored at –20° C. The matrices were washed with 200 μl of D/BB plus 10 mM MgC12 (D/BB=70 mM NaCl, 20 mM Tris-HCl pH 8.0, 20 mM KCl, 0.1% digitonin, 1% thiodiglycol, 50 mM spermine, 125 mM spermidine) and then resuspended in 50 μl of protease buffer (10 mM Tris-HCl pH 8.0, 20 mM EDTA, 0.5% SDS, 0.5 mg/ml proteinase K) and incubated at room temperature overnight. Twenty μl aliquots of the pellet and supernatant fractions were subjected to electrophoresis in a 1% agarose (FMC Sea Kem GTG 50072) gel, prepared and run in TAE (TAE=40 mM Tris-acetate pH 8.0 and 1 mM EDTA). The gel was then treated for 20 minutes in 7% trichloroacetic acid, dried and exposed to X-ray film (Kodak X-OMAT AR). This method of representing the DNA bound to the nuclear matrix is called the 'equal fractions' method, as an equal portion of the DNA from the pellet and the supernatant fractions (e.g., 20%) is applied to the gel. This approach allows direct determination of the amount of a fragment partitioning with the pellet or supernatant; very weak-binding DNA fragments are not scored as MARs.

EXAMPLE 2

Results of Isolation and Testing of Operationally Defined MARs

A random sample of MAR fragments was obtained by purifying matrix associated DNA and cloning these fragments. Five different preparations of nuclear matrices were made using one of five different nucleases. From each preparation, twenty colonies were picked, grown and analyzed for the presence of single inserts. A total of thirty-nine clones were then tested for their ability to rebind to the nuclear matrix. Since all clones were obtained using one of the five cloning strategies, the plasmids obtained using each strategy differ only in the content of their insert. The generalized plasmid maps are summarized in FIG. 1.

Each clone was end labeled and tested for the ability to rebind to the nuclear matrix using the exogenous assay. A previously identified strong binding MAR fragment, ToRB7-6 (Hall et al., *Proc. Natl. Acad. Sci. USA* 88:9320 (1991)), served as a positive control. In each case, the non-binding vector served as an internal negative control. Results of such binding assays are shown in Table 1, which contains a summary of the relative binding strength of all the MAR clones tested. Among the clones obtained from nuclear halos treated with restriction enzymes that have four base pair recognition sites (RsaI and TaqI), 9 of 17 fragments had some binding activity as compared to 14 of 17 clones when enzymes with six base pair recognition sites were used. In addition to the 34 clones represented, five clones from the DnaseI treated nuclear halos were tested (302, 303, 305, 311 and 319); no binding was detected for any of these samples (results not shown). Relative binding strength was based on the proportion of each MAR fragment that partitioned in the bound fraction on a scale of 0 to 100%. In Table 1, no=no detectable binding; weak=detectable –40%; medium=40–70%; strong=70–100%.

TABLE 1

Clones Tested for Matrix Binding Activity*

| Four base cutters | | Six base cutters | |
|---|---|---|---|
| Clone # | Binding strength | Clone # | Binding strength |
| RsaI:EcoRV | | HindIII | |
| 1 | Weak | 201 | weak |
| 2 | Weak | 202 | medium |
| 3 | No | 203 | no |
| 4 | Weak | 205 | medium |
| 6 | no | 206 | weak |
| 7 | weak | 209 | weak |
| 8 | no | 211 | strong |
| 21 | no | 216 | weak |
| 22 | weak | 210 | no |
| 23 | no | 217 | weak |
| 26 | no | 218 | no |
| 27 | no | 219 | weak |
| 28 | weak | 220 | medium |
| TaqI:ClaI | | EcoRI | |
| 11 | No | 109 | weak |
| 15 | Weak | 113 | weak |
| 34 | Weak | 115 | medium |
| 35 | Weak | 116 | strong |

*Relative binding strength is basd on the proportion of each MAR fragment that partitioned into the bound fraction on a scale of 0 to 100%, where no = no detectable binding; weak = detectable - 40% binding; medium = 40%–70% binding; and strong = 70%–100% binding.

Because the fragments were isolated through their association with the nuclear matrix (the operational definition of a MAR), all of the fragments would be expected to rebind to the matrix in the exogenous assay. However, 40% of the clones did not have detectable binding activity. There are several possible explanations for this discrepancy. One such possibility is a cloning artifact. Some of the DNA fragments may have been altered during cloning, resulting in a loss of binding activity. This possibility can be substantiated in at least one case, pS8. In this clone the expected sequence at the ligation site is GATAC, but sequencing revealed GATCA. This indicates that the fragment was altered during the procedure. Since the clone was created by blunt end ligation, it is likely that the fragment was broken during some procedure and quite possible that the resulting fragment had lost its binding capability. Another possibility is that some of the non-MAR DNA was trapped within the nuclear matrix during isolation. This is a rare phenomenon, and would not be expected to result in 40% non-MAR clones. It is also possible that some of the non-binding clones really are bound to the nuclear matrix in vivo but that the sensitivity of the in vitro exogenous assay was not sufficient to detect weak binding fragments (see Materials and Methods for discussion of sensitivity of detection). Another possible explanation for the isolation of operationally defined MAR sequences that did not rebind to the nuclear matrix is their size. Several of the isolated MAR fragments showed significant reduction in binding when cleaved into smaller pieces (data not shown), which supports the hypothesis of a lower size limit for MAR fragments. The clones ranged in size from 150 to 200 base pairs. It is possible that none of the isolated Dnase1 clones had binding activity because they were below the minimum size requirement. Furthermore, a higher percentage of the clones obtained using restriction enzymes with six base pair recognition sites (EcoRI and HindIII) had matrix binding activity (14/17) than those clones obtained using restriction enzymes with four base pair recognition sites (9/17). Again, this subtle discrepancy may be the result of the smaller size of the fragments generated using four base cutters. This observation may also play a part in the strength of binding, since all of the clones isolated using restriction enzymes with four base pair recognition sites were weak binding MARs or had no detectable binding. It should be noted that although there appears to be a lower limit of size, within a population of fragments of the appropriate size (300 bp to several kilobases), there does not appear to be a statistically significant correlation between binding strength and the size of the MAR fragment (see FIG. 5). Finally, some of the non-binding clones may be parts of MARs that were cleaved during isolation. It appears that the binding of MAR DNA to the nuclear matrix may involve extended contact. If a particular sequence is cut within the extended contact region, it is possible that none of the resulting fragments would be able to rebind to the nuclear matrix in the exogenous assay.

EXAMPLE 3

Materials and Methods for Sequence Analysis of MARs

Subcloning and Sequencing

To effectively analyze the sequence of the MAR DNA, DNA that is not necessary for binding must be excluded. Core binding fragments of the MARs were identified by testing the binding of different subfragments of the clones and determining the particular fragments that contained the majority of the binding activity. These fragments were then cloned and sequenced.

A 998 bp fragment of pS116 was excised using MunI and PstI and ligated into the EcoRI and PstI sites of pBluescript II SK+to create pS116-1.1B (SEQ ID NO:5).

A 635 bp and a 1087 bp fragment of pS202 were excised by cleavage with HindIII and EcoRI and ligated into pBC KS+(Stratagene) using the same two restriction enzymes to create pS202-1 (SEQ ID NO:6) and pS202-2 (SEQ ID NO:7), respectively.

A 704 bp fragment of pS205 was excised with EcoRI and HindIII and ligated into the EcoRI and HindIII sites of pBC KS+to create pS205-2 (SEQ ID NO:8).

A 306 bp fragment of pS206 was excised with BamHI and HindIII and ligated into the BamHI and HindIII sites of pBC KS+to create pS206-1 (SEQ ID NO:9).

A 685 bp fragment of pS211 was excised with EcoRI and HindIII and ligated into the EcoRI and HindIII sites of pBC KS+to create pS211-1 (SEQ ID NO:10).

A 899 bp fragment of pS217 was excised with BamHI and ligated into the BamHI site of pBC KS+to create pS217-1 (SEQ ID NO:11).

A 1499 bp fragment of pS220 was excised with XhoI and HindIII and ligated into the XhoI and HindIII sites of pBC KS+to create pS220-1 (SEQ ID NO:13).

All digestions, ligations and transformations were performed according to manufacturer protocols. The maps of the original plasmids and their subdlones are depicted in FIG. 2.

The MAR fragments were sequenced in stages by primer walking. Each clone was sequenced using the Universal-21M13 (TGTAAAACGA CGGCCAGT)(SEQ ID NO:18) and reverse M13 (CAGGAAACCGA TATGACC)(SEQ ID NO:19) primers at Iowa State University Nucleic Acids Facility for the initial portions of the sequence. In the case of longer clones, when a complete sequence was not obtained from the initial sequence, internal primers were designed and then constructed at the Molecular Genetics Facility at North Carolina State University. All interior primers are underlined in FIG. 3. Because of the AT-rich nature of the MARs, primers with suitable melting temperatures, but that avoided secondary structural features, had to be designed. The usefulness of each primer was tested by attempting to amplify an internal MAR fragment using the constructed primer in conjunction with either the universal or reverse primer in a polymerase chain reaction (PCR). PCR was performed using Boehringer Mannheim Taq polymerase according to the manufacturer's protocol. Primers that resulted in successful amplification of DNA were used for additional sequencing at Iowa State University. Sequences of the primers used are underlined within the sequences in FIG. 3.

EXAMPLE 4

MAR Sequences

From the randomly isolated MAR fragments, a sample of ten binding clones (pS1, pS4, pS115, pS116, pS202, pS205, pS206, pS211, pS217 and pS220) and two non-binding clones (pS8 and pS218) were chosen for sequence analysis. These particular MARs were chosen as representatives of the population based on binding strength. Within this population of ten sequences are several weak, medium and strong binding MARs, representing the spectrum of binding strengths within population. The binding of MAR fragments appears to involve multiple protein DNA interactions rather than a single binding site (Gasser et al., 1989), however, it is not known if multiple interactions are required for MAR binding, or if longer MAR fragments simply consist of many smaller MARs each acting independently.

The binding of a particular MAR may be affected when that fragment is cleaved so that shorter fragments may contain none, some or all of the binding potential of the original full-length clone. In some instances, all of the fragments are capable of binding to the nuclear matrix, whereas in others the binding is confined to one of the smaller fragments.

Several of the isolated clones were several kilobases in length. To avoid including non-MAR DNA in our sequence analysis, these samples were digested into smaller fragments and the binding of these subfragments tested. In the case of seven clones (116, 202, 205, 206, 211, 217 and 220) a smaller core binding fragment that maintained the most of the original binding strength was identified. These core binding fragments were subcloned and used instead of the original sequence (see FIG. 2 for plasmid maps). In the case of clone pS202, two binding subfragments (pS202-1 (SEQ ID NO:6) and pS202-2 (SEQ ID NO:7)) were identified, each of which maintained a binding strength similar to that of the original clone. Both fragments are included in this study. The other three clones (pS1, pS4, and pS115) were sequenced in their entirety (SEQ ID NO:1, SEQ ID NO:2, and SEQ ID NO:4, respectively). Two of the three non-binding clones (pS8 and pS218) were sequenced in their entirety (SEQ ID NO:3 and SEQ ID NO:12, respectively). The binding strengths of the subclones were rated on a scale of 0–100 based on the percent of the MAR that partitioned in the bound fraction in the standard exogenous assay (FIG. 4).

EXAMPLE 5

Motif Significance in MAR Sequences

Several different motifs have previously been identified as associated with MAR sequences, including A boxes (SEQ ID NO:14), T boxes (SEQ ID NO:15), ARS consensus (SEQ ID NO:16), and the Drosophila consensus sequence for topoisomerase II (SEQ ID NO:17). A search was conducted for the presence of these motifs using the Apple MacIntosh program MacVector. In the search, 1 mismatch was allowed in the cases of the ARS consensus and T box, and 2 mismatches in the cases of A box and the consensus for topoisomerase II. Allowing for this number of mismatches results in similar probabilities of occurrence for all four motifs (see Table 2). The A box and T box motifs often resulted in overlapping regions due to their AT-rich nature. For example, within a stretch of 20 bases of Ts, 10 T boxes can be found. The probability of finding an additional T box upon inclusion of the next base is 0.35 in a region of DNA that contains 70% AT. To avoid this artificial identification of additional motifs, only two T boxes would be counted in the above example.

In the MAR DNA fragments obtained from the random cloning procedures described in the above Examples, AT rich motifs were present. These AT rich regions are depicted in FIG. 4. Additionally, several of the randomly obtained MAR sequences contained short stretches (20 bp) of highly AT rich ($\geq 90\%$) DNA. The locations of these stretches are also shown in FIG. 4.

The present inventors tested the occurrence of each of these motifs for statistical significance against the number of occurrences that would be expected at random, to determine if these motifs are over-represented in MAR DNA. The probability of the presence of a specific sequence starting at a specific base within 70% AT rich DNA was calculated by multiplying the probabilities of each base in the motif (0.35 for A and T, 0.15 for G and C). Since mismatches of 1 or 2 bases were allowed for certain motifs, the probabilities were adjusted by dividing the calculated probability of occurrence of the motif with no mismatches by the lowest probability of an individual base (or bases when two mismatches were allowed) within the motif, yielding a conservative estimate of probability. In addition, the probabilities were multiplied by a factor of two, since these motifs can occur in either strand of the DNA. Although the two strands of a DNA sequence are not independent, the factor of two provides a simple and conservative method for calculating the expected frequency within double stranded DNA. For example, the probability of the topoisomerase II consensus sequence (GTNWAYATTNATNNR) (SEQ ID NO:17) occurring in 70% AT rich DNA without any mismatches is calculated by multiplying the expected frequency of each base together: [(0.15)(0.35)(1)(0.7)(0.35)(0.5)(0.35)(0.35)(0.35)(0.35)(1) (0.35) (0.35)(1)(1)(0.5)]=$1.68 \times 10^{-5}$.

This calculated probability is then adjusted for the allowance of up to two mismatches by dividing by 0.15 and 0.35, the two lowest expected frequencies of each base. The resulting value is then multiplied by two, since motifs can occur in either strand of DNA. The calculated probability for an A box with two mismatches, an ARS consensus with 1 mismatch, and the consensus for topoisomerase II with two mismatches are coincidentally identical, $6.428 \times 10^{-4}$, whereas the calculated probability of a T box occurring with one mismatch is slightly higher, $1.26 \times 10^{-3}$. The probability of the occurrence of a 20 bp stretch of DNA containing 90% or greater AT content, was calculated by taking the probability of a single base being either A or T (0.7) to the $18^{th}$ power. Therefore, the probability of occurrence of a twenty base pair stretch with two mismatches (or 90% AT rich DNA) is equal to $1.628 \times 10^{-3}$. Since this type of motif will automatically be present on both strands at the same time, only those motifs found in one strand were counted. As with the other motifs, overlapping regions were not counted as separate occurrences, however, this motif often occurs in stretches much longer than 20 bp. The actual lengths of the regions are depicted in FIG. 4. The number of occurrences were counted as one from 20–39 bp; two from 40–59 bp; and so on. The probability of a motif starting at any one site, was converted to an expected number of occurrences within a DNA sequence by multiplying by the number of base pairs in its length.

For purposes of the calculations the probability of a particular base occurring at a particular site was assumed to follow a multinomial distribution, i.e., any of the four bases can occur at a particular site. Note that this assumption may not be true if there are restraints on DNA sequences (e.g., five consecutive Gs not allowed), but since such restraints are presently unknown, the assumption of multinomial distribution was made. It would be expected that the probability of a particular string of bases (a motif) occurring at a particular site to have approximately a normal distribution. The observed number of MAR motifs were compared to the number expected under this normal distribution assumption. The number of observed MAR motifs was significantly greater (at the 1% level) than the number expected if the observed number of MAR motifs is greater than a calculated critical value. The critical value is $\mu+Z_{0.01}\sigma$ (Steele and Torrie, *Principles and Procedures of Statistics: A Biometrical Approach,* McGraw-Hill Publishing Co., New York, N.Y. (1980)). In this equation $\mu$ is the expected number of MAR motifs, $Z_{0.01}$ is the Z statistic at 1% and $\sigma$ is the standard deviation of the expected number of occurrences of MAR motifs given a random expected number of occurrences given a random sequence of bases ($\sigma=\sqrt{\mu}$). The motifs in question have already been shown to be associated with certain MAR sequences. The null hypothesis of the motifs occurring at random is compared to the one tailed test of the alternative hypothesis, that these motifs occur more often than would be expected by random occurrence. The 1% critical values are shown in Table 2. Since the observed number of occurrences for all five motifs is greater than the critical values, the null hypothesis can be rejected in favor of the alternative hypothesis that these motifs occur more often in MAR DNA than would be expected by chance alone. A boxes, T boxes, ARS consensus, topoisomerase II consensus and 20 bp regions of ≧90% AT DNA all occur more often than would be expected at random.

| Clone | length bp | A box −2 6.428 × 10−4 obs | exp | ARS con −1 6,428 × 10−4 obs | exp | T box −1 1,261 × 10−3 obs | exp | Topo II-2 6,428 × 10−4 obs | exp | 90% A+T 1,28 × 10−3 obs | exp |
|---|---|---|---|---|---|---|---|---|---|---|---|
| pS1 | 437 | 9 | 0.280 | 0 | 0.280 | 3 | 0.551 | 1 | 0.280 | 7 | 0.711 |
| pS4 | 587 | 7 | 0.377 | 2 | 0.377 | 4 | 0.740 | 2 | 0.377 | 4 | 0.955 |
| pS115 | 866 | 4 | 0.556 | 2 | 0.556 | 5 | 1.092 | 0 | 0.556 | 4 | 1.409 |
| pS116-1.1B | 998 | 11 | 0.642 | 1 | 0.642 | 14 | 1.258 | 2 | 0.642 | 16 | 1.624 |
| pS202-1 | 635 | 7 | 0.408 | 0 | 0.408 | 4 | 0.800 | 1 | 0.408 | 3 | 1.033 |
| pS202-2 | 1087 | 7 | 0.698 | 3 | 0.698 | 4 | 1.370 | 2 | 0.698 | 3 | 1.769 |
| pS205-2 | 704 | 9 | 0.452 | 4 | 0.452 | 5 | 0.887 | 2 | 0.452 | 9 | 1.146 |
| pS206-1 | 306 | 5 | 0.196 | 1 | 0.196 | 2 | 0.385 | 1 | 0.196 | 5 | 0.498 |
| pS211-1 | 685 | 7 | 0.440 | 2 | 0.440 | 11 | 0.863 | 4 | 0.440 | 9 | 1.115 |
| pS217-1 | 899 | 10 | 0.578 | 2 | 0.578 | 5 | 1.133 | 1 | 0.578 | 2 | 1.463 |
| pS220-1 | 1499 | 21 | 0.963 | 5 | 0.963 | 10 | 1.890 | 2 | 0.963 | 20 | 2.440 |
| Total | 8705 | 97 | 5.599 | 22 | 5.599 | 67 | 10.974 | 18 | 5.599 | 82 | 14.171 |
| 1% Critical Value | | 11.10 | | 11.10 | | 18.67 | | 11.10 | | 22.92 | |
| Other MARS | | | | | | | | | | | |
| ARS-1 | 838 | 5 | 0.538 | 2 | 0.538 | 2 | 1.056 | 0 | 0.538 | 1 | 1.364 |
| ToRB7-6 Sca/Cla | 1103 | 13 | 0.709 | 3 | 0.709 | 7 | 1.390 | 3 | 0.709 | 16 | 1.795 |
| Non-binding clones | | | | | | | | | | | |
| pS8 | 383 | 2 | 0.246 | 0 | 0.246 | 1 | 0.482 | 2 | 0.246 | 2 | 0.623 |
| pS218 | 999 | 5 | 0.642 | 2 | 0.642 | 5 | 1.259 | 4 | 0.642 | 0 | 1.626 |

EXAMPLE 5

Motif Frequency and Binding Strength

To determine if a correlation exists between the number of these motifs present within a particular MAR sequence and its binding strength, that data (FIGS. 6–11) was plotted and tested the significance of the regression coefficient, r, using an F test (Steele and Torrie, 1980). Included were all eleven binding sequences (SEQ ID NOS:1, 2, 4–11, and 13); two non-binding sequences (SEQ ID NO:3 and SEQ ID NO:12); and two well characterized MARs (ToRB7-6 and ARS-1).

The correlation between binding strength and the length of the MAR as well as the % AT content of MARs was analyzed. The analysis (Table 3), shows a significant correlation between the number of 20 bp stretches of 90% or greater AT and the binding strength of MARS. The number of T boxes is also significant, as is the number of A boxes. No significant correlation between binding strength and the length of the MAR fragment nor the presence of any of the other MAR related motifs was detected in this analysis. However, there was a significant relationship between binding strength and overall AT content. This is the first report of a correlation between the abundance of certain MAR related motifs and MAR binding strength. In addition, the newly identified MAR related motif of local AT rich regions (≧90%), has a higher correlation to MAR binding strength than any of the previously identified motifs.

TABLE 3

| Motif | R | F calc | significance |
|---|---|---|---|
| % AT | 0.77 | 18.93 | ** |
| length | 0.38 | 2.19 | ns |
| # A box/kbp | 0.19 | 0.49 | ns |
| total # A box | 0.57 | 6.48 | * |
| # ARS/kbp | 0.29 | 1.27 | ns |
| total # ARS box | 0.35 | 1.85 | ns |
| # T box/kbp | 0.64 | 9.45 | ** |
| total # T box | 0.76 | 17.98 | ** |
| # TopoII/kbp | 0.06 | 0.04 | ns |
| total # TopoII | 0.23 | 0.07 | ns |
| # 90% AT/kbp | 0.69 | 12.07 | ** |
| total # 90% AT | 0.80 | 24.62 | ** |

$$r = \text{regression coefficient} = \frac{[3XY - (3X3Y)/n]}{(3X^2 - [(3X)^2/n])(3Y^2 - [(3Y)^2/n])}$$

Fcalc = F statistic = $(n-2)[r^2/1-r^2)]$
ns = not significant
*= significant at 95%
**= significant at 99%

The relationship between certain MAR related motifs and MAR binding strength suggests that these motifs are general components of MARs. The lack of this relationship for other motifs suggests that these sequences are over-represented without being associated with MAR function, or may be related to only certain categories of MARs. In addition several other MAR related motifs (such as the asymmetric GA-rich stretches, or homopurine stretches) are found within some, but not all of the randomly obtained sequences. The presence of such a motif may indicate a specific class of MARs, but since there is no information about the location of these random sequences within the genome, it cannot be inferred from the presence of this motif that a sequence is a MAR with a specific function (or even a MAR at all).

MARs may interact with the nuclear matrix through a variety of secondary structure motifs including a narrow minor groove, transiently single stranded regions and bent DNA. These structural motifs are expected to be present in the MARs described here because of their high AT content. A narrow minor groove is a feature of DNA containing long A tracts, a predicted feature within high AT content DNA.

EXAMPLE 5

Increasing Average Expression Levels

Earlier studies (Allen et al., *Plant Cell* 5:603 (1993)) showed that flanking a GUS reporter gene with two copies of a yeast MAR element (ARS-1) increased average GUS expression by 12-fold in stably transformed cell lines. In the present Example, the same cell line is transformed with constructs similar to those of Allen et al., 1993, but using a MAR having a sequence selected from SEQ ID NOS:1, 2, 4–11 and 13.

Transformation is achieved by mixing the appropriate reporter test plasmid and a selection plasmid, co-precipitating them onto microprojectiles, and bombarding plates of tobacco suspension culture cells as described previously (Allen et al., 1993). Antibiotic-resistant microcalli are selected and each callus is used to start an independent suspension culture cell line. Histochemical staining of segments from the original microcalli show that the staining intensity is greater in cell lines transformed with MAR plasmids. After several weeks of growth, with weekly transfers, suspension cells are harvested, DNA is extracted from each cell line for Southern analysis and quantitative PCR assays, and portions of the same cell population are used to measure extractable reporter activity and expressed protein levels. Transgene copy number estimates and expression data are calculated. Levels of GUS gene expression, measured as GUS enzyme activity, are assessed and compared to controls.

The foregoing examples are illustrative of the present invention, and are not to be construed as limiting thereof. The invention is described by the following claims, with equivalents of the claims to be included therein.

That which is claimed is:

1. An isolated DNA molecule having a nucleotide sequence selected from the group consisting of:
   (a) SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:13; and
   (b) sequences that hybridize to the isolated DNA of (a) above under conditions represented by a wash stringency of 0.3M NaCl, 0.03M sodium citrate, and 0.1% SDS at 60° C., and which encode a matrix attachment region.

2. A DNA construct comprising:
   (a) a transcription initiation region and a structural gene positioned downstream from said transcription initiation region and operatively associated therewith; and
   (b) the matrix attachment region according to claim 1 positioned either 5' to said transcription initiation region or 3' to said structural gene.

3. The DNA construct according to claim 2, wherein said matrix attachment region is 5' to said transcription initiation region.

4. The DNA construct according to claim 2, wherein said matrix attachment region is 3' to said structural gene.

5. The DNA construct according to claim 2, further comprising a second matrix attachment region that differs in sequence from said matrix attachment region according to claim 1.

6. A DNA construct comprising:
   (a) a transcription initiation region and a structural gene positioned downstream from said transcription initiation region and operatively associated therewith;
   (b) a matrix attachment region according to claim 1 positioned either 5' to said transcription initiation region or 3' to said structural gene; and
   (c) a second matrix attachment region according to claim 1, wherein said second matrix attachment region is positioned either 5' to said transcription initiation region or 3' to said structural gene.

7. The DNA construct according to claim 2, further comprising a termination sequence positioned downstream from said structural gene and operatively associated therewith.

8. The DNA construct according to claim 6, wherein said first and said second matrix attachment regions differ in sequence.

9. A vector comprising the DNA construct according to claim 2.

10. The vector according to claim 9, wherein said vector is selected from the group consisting of plasmids, viruses, and plant transformation vectors.

11. An in vitro host cell containing the DNA construct according to claim 2.

12. An in vitro host cell according to claim 9, wherein said host cell is an animal cell or a plant cell.

13. A transgenic plant comprising transformed plant cells, said transformed plant cells containing the DNA construct according to claim 2.

14. The transgenic plant according to claim 13, which is a monocot.

15. The transgenic plant according to claim 13, which is a dicot.

16. The transgenic plant according to claim 13, which plant is a dicot selected from the group consisting of tobacco, potato, soybean, peanuts, cotton, and vegetable crops.

17. A DNA construct comprising a transcription initiation region, a structural gene positioned 3' to said transcription initiation region and operatively associated therewith, and a matrix attachment region positioned either 5' to said transcription initiation region or 3' to said structural gene, wherein said matrix attachment region has a sequence selected from the group consisting of SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:13;

said DNA construct carried by a plant transformation vector.

18. The DNA construct according to claim 17, further comprising a second matrix attachment region that differs in sequence from said matrix attachment region, wherein said second matrix attachment region has a sequence selected from the group consisting of SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:13.

19. A recombinant tobacco plant comprising transformed tobacco plant cells, said transformed tobacco plant cells containing a heterologous DNA construct comprising a transcription initiation region functional in plant cells, a structural gene positioned 3' to said transcription initiation region and operatively associated therewith, and a matrix attachment region positioned either 5' to said transcription initiation region or 3' to said structural gene, wherein said matrix attachment region has a sequence selected from the group consisting of SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:13.

* * * * *

SEQUENCE LISTING

<160> NUMBER OF SEQ ID NOS: 22

<210> SEQ ID NO 1
<211> LENGTH: 437
<212> TYPE: DNA
<213> ORGANISM: Nicotiana tabacum

<400> SEQUENCE: 1

```
gatacgtaaa caacgtgtat ccagtaagta tcaagcctaa tctcgaagtg gtagagacga      60
gatgaccgac tttgacactc actatgggtc aataataata actgaaataa aactaagata     120
tttaaaccaa catgatttac agaatttaca ataatttatt taatcagcag aaataatcaa     180
atttcttcaa atgtaacaat tctcaatata ttaattaaat tccttcaatt caaataattt     240
ctaatttatc aattaaacct catttacagg agtaacaatt aattccttaa caagcaagaa     300
taataattca ttaaattcca aggatttttc aatttattaa ttagcttcac aacctgaaat     360
aaattattaa agtatcgtgt aattattatt attaagcacg atttctgccg aggacatacg     420
gcccgatcca gagtatc                                                    437
```

<210> SEQ ID NO 2

<211> LENGTH: 587
<212> TYPE: DNA
<213> ORGANISM: Nicotiana tabacum

<400> SEQUENCE: 2

```
gatactagag tggtgttatc aattcttact cgtatgaatt aattaaattt gtctcttatt      60
tctgtcctaa gtcatataca agaaatgcta actccatccg tttcaatccc tatgacatag     120
tttgatttga ttgaatttga aaatttaaga aacaaaagat aattttttgtg actcataatt    180
tagacatgtg ttataagact tttctcatga attttttaga aacaaatgat aattttttgga    240
actcataatt tagacgtttt ataaaaaata ctaactgcat ctggttcaat atttatgtgt     300
tattcctata aaacttctgg acttatattt ttaaatattt cataatattt ggtatcggta     360
taattttttt gtcactttttg gatgaaaggg aagtttaagt aaatttctttt ttccaaattt   420
agaaagttat aatattctttt ttaaaacgcc caaaaagaaaa aataagctat tgattattat   480
aagcctaaac caaaagaatt ctttgactag taggaagcca tttttaagtt aggcgccaaa     540
attcaaagcc aacgtgggca tatctccaaa ctggcggcta cagtatc                   587
```

<210> SEQ ID NO 3
<211> LENGTH: 383
<212> TYPE: DNA
<213> ORGANISM: Nicotiana tabacum

<400> SEQUENCE: 3

```
accgctttta ttattattat ttttaccgag aattacaaca tcatgaaaat acatctcgaa     60
ccacgtcaca tcaatgcacc cgcggttatt gacatatttc aactctgttg agatttggat    120
ttgggtcaca taaatgtgca cccgagttta agaggataac attattaaat acgcgcctaa    180
aacgactagc gtatcattat tttgggtagg gccgtgaaat tttgctaaac tgcccatcca    240
gaaatctaag taattttacc aacacgtata gagggcccca cagcttgtgt attttttgtt    300
gtcgaggctc gtctcattca ttattttttaa aaggaatttg caacgtcgtg gaaatgcatc   360
tcgaaccacg tcacaatcaa tga                                            383
```

<210> SEQ ID NO 4
<211> LENGTH: 866
<212> TYPE: DNA
<213> ORGANISM: Nicotiana tabacum

<400> SEQUENCE: 4

```
gaattcgata gactcactta aatattagaa gtgaattacc tagagttaga tccaaaacaa     60
ttatcttgca cctatcctat caacccttat cttttcccat tgattactac cttgcttacc    120
tttgttacga ttttcattag acaataactt tagattctta gttaattgca gttagaaatt    180
atattaaatt tcaattgttg gatcatcttg aataccaatc aagctagaaa atacaagaat    240
actgtttaaa tcaaatccat gtggatacga tattatacta tattatattt gacttgtgag    300
cattatttat gtgtgttttg tgctcgtcaa agtttggcgt cgttgccgag gattggcaat    360
caatagtgtt tgaaatagtt tttggtgcta atttaggaat taggttttat ttatttattt    420
tttctttttct tttcttttttc cttttctatt ttatttcctt tattagttaa cttcttttca    480
agatttttttt tgtagtacct aacaagttag agaagatact gtagattttg aactctaaat    540
gttgtgaaga tggagtacaa ccagcctaag aaaatatttg aatagttagc agctgaacat    600
tatcggcggt cggttatgcg gtttaaatgc ggtggaagca tctaccaccg cagcctaaag    660
aaaatatttt gaatagttag cagcttgaac attatcggcg gtcggttatg tgttttaaat    720
```

```
gcggtggaaa tcatctacgg gctaactgtc aagcaggtat gtattcttcc tatggttcgt     780
attttgagga gtctcactct gtttctagtt cgtacatgta tgaggattca tatgggcaca     840
actctgactc tggttgggat gaattc                                          866
```

<210> SEQ ID NO 5
<211> LENGTH: 998
<212> TYPE: DNA
<213> ORGANISM: Nicotiana tabacum

<400> SEQUENCE: 5

```
gaattgtatt attgttaggt gggagagatt tttgactata tgggttaaaa tcagcgacaa      60
agggccaaat atacctattt acttttaaaa atagtctaat ataacctctc gttatattat     120
taggttatct atacctttgc agtcatattt tgggttcaaa tataccctc atttaaacgg      180 agggacacgt gtcatcgtcc tgttggtcaa ttctaaatat ctcctaatta attaaaaaga    240
ctcattaccc atatccgaaa atatttttt aaagcaatat ttttttataa aaatggaaa      300 aactgaaatt attttacta aaaattgaaa aaacgaaaa tagttttttt tcagtttta       360 caaaaaaact attttagaaa aaattgaaaa atattttcta aaacaatgtt tttgtaaaaa    420
ctgaaaaaaa agaagctgaa atcaattttt ctaaagcaat tttatttgta aaatctggaa    480
aaaactacta aaaactgaaa aaatgaaaat attttttttt ctaattttta caaaaaaaac    540
tgctttaaaa aaagctgaaa atattttcta aaacaatatt tttgtaaaaa ctaaaaaaa    600 aatattttct tctttttttc agtttttagt taaaaatatt taagttttt ccagttttta    660 attactttag aaaattactt ttctgctttt ttttcagttt ttacaaaaat attattttag     720 aaaatattt tcagttcttt aaagcagttt ttttttgtaa aaacttgaaa aacaatattt     780 tcgtttttt cagtttttag taaaatttgt ttttagtttt tttcagtttt taccaaaaat    840
aaaattgctt tagaaaatta ttttcgggt atgggtaatg ggtcttttta attaattagg    900
agatattttg aattgatcaa taggacgatg acacatgtcc ctccgtttaa atgaggtgta    960
tatttgaatc caaagtaaga ctgcagcccg ggggatcc                             998
```

<210> SEQ ID NO 6
<211> LENGTH: 635
<212> TYPE: DNA
<213> ORGANISM: Nicotiana tabacum

<400> SEQUENCE: 6

```
gaattcgata tggcttgttg acaagaatt aatgaatcaa ttgtgaaaaa gttgatggac       60
atattgaagg taaatcata tactattttt ctaaatctc ttttaaatgt tccccaatta      120
tctgatttct atattgctct taaatgtcac tcaaccttag atcaacaaac ataaactta     180 cccagtacat aagagattgc ggcattatgg cttgaagaaa atcctagaga cacatctgca    240 ccacatatt gaatttatac ccacagtaat agagctcggt tagtacatta ttattatgga    300
tgttacgatc cgttgcagta tccattatta ttttccttcg gtgaaaatgg atgacattgt    360
ggaattaaaa aaattattca gacaaaaaat tcgacgaaac gtagagctta ctgcgaacat    420
gaacaattgc ccagtatatc aaatacgtgt tcagttgatg gattccttga tatggaagat    480
gaatcactac aaagaggaaa acgaaaaaga gatacagtgt cttgtcgaga gtattattgt    540
tacaaatttc aactaagaaa taatgaaaca atgaagtgta cattgtggg gagaatattc     600 caacaattta tagtagatat atatatataa agctt                                635
```

<210> SEQ ID NO 7
<211> LENGTH: 1087
<212> TYPE: DNA
<213> ORGANISM: Nicotiana tabacum

<400> SEQUENCE: 7

```
aagcttgcac gcctacatcg tgggataatt tagaaaaagg aaagggtata ttggatcccc      60
ctatcatttg tgaaacaggt aaccatacga gaaccccttt cgcttcctga aaaatgttat    120
atattgttgt actcatattt atacactatt tattattaat ataacgatgc ttattttgct    180
tggagattgg agattatcac agcttattta tcttatattg tatcttatta aacttaaaaa    240
cataaatact acgtgctctt ttaatttggg atctattaag ggttcgttgc acgcttttaa    300
acatcttggc tattctgttt accagctgct accttagcct gtatgcttac atcatctcct    360
aatttagaca aaggaaaggg tatattggac cccccctatc attcgtgaaa caggtaaaca    420
tacattcaga ttatactctt ttcagaatga catattgttt atacattact gtaaattgtg    480
actatttgta tattagggtc cacatcgggt acatctaacc tgcgtcatgt tatcttgaac    540
actgttccaa tcaaaggttt gcacaaactt aatgttacaa tcatgtccac catacgtatg    600
ccttggtgct cttttttttc ctaatgatac ttcttatata ttcagctcat aggcgggcca    660
gaaaggtgtg cctggtcact aaagagcaac gaagtgagta tgttgctcta aaaagggtcc    720
cacactgtca attctgtcat ccaaagaagt ttgaatatga acctccagga ttttgctgta    780
acagtggttc ataaggttg acatctcata aaatgccaac tgaattatcg gagttatact    840
ttggaaatac tgaagaatct gaaaattttc gaacttatat tagaacatac aataacatgt    900
ttgcatttac ttcacttggt gtcaagtatg ataaagagct agcgagaaga aattgtggta    960
tctacacatt tagagtccag ggacagatgt atcattttat agatgattta gttccttcca   1020
atgaaaaacc taggaattta tagctgtact tctacgataa tgataatgaa ctagccaaat   1080
caagctt                                                             1087
```

<210> SEQ ID NO 8
<211> LENGTH: 704
<212> TYPE: DNA
<213> ORGANISM: Nicotiana tabacum

<400> SEQUENCE: 8

```
gaattcttca gccattgtac atatagttgt gtattaatgt tattaataat ggataattaa      60
atatatacct ggaataaata tacgatatta taatagtgtg taattatata taaaaattat    120
acataatata atgatggtat ttaatatagc ataaatttga acgatctgga ttgatttctt    180
gaatcaaaat agagttgtgt gaaaagaaaa gaatgagatg aaaagcaaag tatgaagaga    240
tgaatttgtg tttttttat ggaggaggaa ggttctcagt gatggaatca tccctggttt    300
tctttagcac caatgaaagt aatgaacccc ccccaaaaaa aaaaaaaaaa aaaaaaaagg    360
gagagagagt agaatggaac ggctaggtga agtatagga gtagaaatta ggttcaggga    420
gagaaaaggg gggaaattaa ttcctaaatt aatgggattc taattttaa actgttttga    480
aatattttaa aagtagtgtt atttatatta ttaactttta aaaaaagtca aacgaggtaa    540
aaattccatg ggggaaaatt taaatggtta gtcttctata atattttcaa ctctgcttag    600
cactaaaaat tagtctaaaa ataacccctaa attagtgtat ctaaattaat tagttcatcg    660
aacaggagca ttggattatc cctccagagt tacacaggaa gctt                     704
```

<210> SEQ ID NO 9
<211> LENGTH: 306
<212> TYPE: DNA
<213> ORGANISM: Nicotiana tabacum

<400> SEQUENCE: 9

```
ggatccagct attattatag catgtgagtt gtccgtgaac agctaatttt ttaccacacc    60
caaattcaat actattttag tgtaaatata tcttttaggt ctagtcttaa tatttaactt   120
tttgtcttac ttttaataga ttttatttga gaaaaattaa taattacaaa aaataaaaag   180
tatatattca catacttata gtacaaactt tgtttctatt tataaagaga aaagaaatt    240
ttacaaaaaa caaatatatt tgctttcttt taattagtag ttttattaag caagctatag   300
aagctc                                                             306
```

<210> SEQ ID NO 10
<211> LENGTH: 685
<212> TYPE: DNA
<213> ORGANISM: Nicotiana tabacum

<400> SEQUENCE: 10

```
gaattccgtg gttttagcac ggtcgctcaa ttgtcatatt tggctcattt atctgatttt    60
taaacaatta agaacttata tgcaaattta acttttaaaa ccgcttttat cattatttat   120
tttatacaaa attcaacgt cgtgaaaagg catctcgaac cacgccacaa ccagtgcaca    180
cgtgatttgt tgacgcattt tggacttcgt caagatcgtg atttgggtta cataaatgta   240
caccccgtat ttaagaaaat aaccttatta atattgcgc caaatacta cgcgttatga    300
tactattagg gtaggcttgt gaattttact aaatcgccca tctcggaatc taggtatttt   360
cttatattaa aaaaaataag atgggggcct gcaattttt attatttaat atttatttat   420
tttttagcga agatccctcc ttatttttat gaatacccctt taatgactac atctttatta   480
ttactaagtt tgtctataat tatgaagtca atctctacat acataaaaat aacatattaa   540
ttactaattt aaaacaaata ttaatggaaa gtaatattac taaaattata attacaaaca   600
acatggaatt gtcacaaaat aaaaaataaa aactaattat cccatagttg gattaaaatt   660
catattgtta gtatgactta agctt                                        685
```

<210> SEQ ID NO 11
<211> LENGTH: 899
<212> TYPE: DNA
<213> ORGANISM: Nicotiana tabacum

<400> SEQUENCE: 11

```
aagctttaaa aggaagagag ccacaatttt ctttgacctt ccttctctcc tagccactaa    60
gatatacagt actggtcaaa aagagcatat ttatagctca aaattttgcc ttttctgtt   120
gtaaacgtga ttgtttctta cttggattct tgttctatat atttacggga gaaagagca   180
atttgcatgc tcctaaatct tttattttct ggtgaaaaat tggtctttaa ttggctggga   240
attattttt agatgctaca accttgacaa acacctaaga atattttagt gacaatggct   300
tgttctttga gtactggttt ttctgttct ggtccctgtt tcaacgccac agccaaagag   360
tctcgtcgtc attgcccttc gattggcact ctgcaactta agatttagc atccagaaa   420
tttctaggca aacccttgga ttatgcatca gatcatattg gtactaacca ttggaatgtt   480
gaacgacttc tgtatgtaa atctctgata catttgcttc tgtgtttata cttggtgttt   540
tcatgttttc attcttgttt taaattttc gagatcaaat catttataag tatttattct   600
```

-continued

| | |
|---|---|
| aatgatttta ggcacaagta tcaatcgctg ctcagagatg gtgggagaag acccttaaac | 660 |
| ccaacatggt agagatcaat tcagcaacac aacttgttga ttcattatta aaagctggta | 720 |
| atagattggt cataattgac ttcttctctc ctagctgtag aggtttcaag actttacatc | 780 |
| ctaaggtaag atatatagca atcccctaaa aaaaaaaaaa aaaaaaaaaa aaaccaacaa | 840 |
| ctacatcgta atcctaagca agttagggtt aactatatga atcatcacta gacggatcc | 899 |

<210> SEQ ID NO 12
<211> LENGTH: 999
<212> TYPE: DNA
<213> ORGANISM: Nicotiana tabacum

<400> SEQUENCE: 12

| | |
|---|---|
| aagcttaact ttactcacat tgctttcttt agggaagcgt cttcttaaat gaccatcctc | 60 |
| taaatttctc atgaatcttc ttctgttgtc cactctgtta tcgctgaaac gaaatctgaa | 120 |
| attgtcatga tgctgactat tatccaatca ctcagtctct aattcatatt tagattatct | 180 |
| tgttcaccag cccatactga ttttattgt tttgggtct aacttttcct tccggtagtc | 240 |
| ggttggagtc atgaacttat ttcttgaaat gaggatatga ctttatggcc tatactcttt | 300 |
| tggtgtctca aggcctgtca cctctcatct tttccttcaa ttgactatag actctgtaat | 360 |
| actgtcatct ttgggatcta ccgttgtcct ccatgtatca tatcttactc ataatgcttc | 420 |
| attaactatt ttcttatttc ccgctaacat ttatgtctat cactttattc tgaaaactcg | 480 |
| aacaagacat tcttttcgtt ttagatcccc tttgctccat ccagtggttc ttcggggac | 540 |
| ttaacgttct cgctctccta gggaggcgag ccacactaag gtaatattta tcccttctag | 600 |
| gctttccgtg cctatcttct gagatatttt tttcatgcta atattcacat ctaattgtaa | 660 |
| ttttctagag tgcgccatct gggtgcctca caagaagagc tattagcatc tttgtaatat | 720 |
| ccttcggaaa tgtcaactaa cacaacacaa tccattcacc attttgggtt actctaacct | 780 |
| cagtcggata ctaatatcct gtcattttat taaactacac atgttagccc ccaataggat | 840 |
| ataactaaga tgggtgtggc caattctaca tacatctgtt actgttgaaa gtaagtcgca | 900 |
| atgctttat ttttctgccg gagttgaaaa taccgataat ctatattaac tgggtacctc | 960 |
| gtacccttct catctttctc cttttacttg ttgaagctt | 999 |

<210> SEQ ID NO 13
<211> LENGTH: 1499
<212> TYPE: DNA
<213> ORGANISM: Nicotiana tabacum

<400> SEQUENCE: 13

| | |
|---|---|
| aagcttgaaa agaagaatt aaggcttgct ttcttaattt ttaaaaaata aaattattt | 60 |
| tgaactatct atactatatt aaaagcacga aaccctatc gaaatgtcgt tcgccttttt | 120 |
| tacccttaa aaataatttt acattagaca aaatagtcat tttactattt ttcctaatat | 180 |
| ataggatttt aaaattaatt taactttggc tattaaacat tttcttataa cttgaaatat | 240 |
| gtaaaactcc taatatttag aaatttaatt aacataacca aggattttta tatcggtaat | 300 |
| aactctaata tggtatccaa atcagtctag aactctctta cctctaataa gtaaaagtac | 360 |
| ttctaataaa ttcatatact ttttctctct tctccgatct ctctttgctc ttcttttat | 420 |
| gtatcctttc ctttctaata gccttttatg agaagtaaac ttttagggtt ggccccccct | 480 |
| cccccacaa ttatatagtt tcttactcag ttgttggaat ataattcaaa ttcttaaata | 540 |
| attgacggtg acattgagtt ttactttgtg gaagagaatt agattctcgt gttagtaaaa | 600 |

```
tcggttagta attgatgatg cattattttt actctataat agagatgcaa ttttattttt      660
gcattttggg atcaaattgt aatgcagtca tatattgatt tcataaatgt ttgggatatt      720
gttggttatt taactagaaa tagacttctt atttcatatt tattgttaaa atcctttatt      780
ggagatgaat tatttgttca ccgattagaa gttgatagtc gcttttgttt tagaagaaat      840
tttaccgtag accaagttaa ggagttttag aagcactttg catgggagca ttagtgtatg      900
ttatggcttt atcaaatata ggttttgaag attcagagag ccaagaaaag ctagaaccca      960
agaactagga agttagagta attcacaata ccataacgtg atataaaact ttttattgta     1020
actcaaatcg gtaatatttt ttgctttagt cttaatcgat aaattatttt tttatattga     1080
ttagttatag gaggctcaca aagttgggaa taattaaaat atcatatttt gtatttgaac     1140
aatttatgaa atagtaattg gtaaaaaatc actttaaatt tttatcctat atccagaagg     1200
attatggtgt ctggcatagt tgtttggaag atttgaatca gggtaaaagt atgttgtaat     1260
ttttattttg ttataggcat tttttgtgct tgattgtttt gttgtcatta tatttatta      1320 tttggaagtg tatatatatg tttgattaaa atatagataa tcaattttat aagaaatttg     1380
caacaattac acaaggataa agtctacaat atgcgagtaa aatttgattg aacctaggat     1440
gtcatattta atgcatattt tatttcaatg tgtttattat acatctattg tattatatg     1499
```

<210> SEQ ID NO 14
<211> LENGTH: 10
<212> TYPE: DNA
<213> ORGANISM: Nicotiana tabacum

<400> SEQUENCE: 14 aataaayaaa                                                             10

<210> SEQ ID NO 15
<211> LENGTH: 10
<212> TYPE: DNA
<213> ORGANISM: Nicotiana tabacum

<400> SEQUENCE: 15 ttwtwttwtt                                                             10

<210> SEQ ID NO 16
<211> LENGTH: 11
<212> TYPE: DNA
<213> ORGANISM: Nicotiana tabacum

<400> SEQUENCE: 16
wtttatrttt w                                                           11

<210> SEQ ID NO 17
<211> LENGTH: 15
<212> TYPE: DNA
<213> ORGANISM: Nicotiana tabacum
<220> FEATURE:
<223> OTHER INFORMATION: n in nucleotide positions  3, 10, 13, and 14
      represents any nucleotide

<400> SEQUENCE: 17
gtnwayattn atnnr                                                       15

<210> SEQ ID NO 18
<211> LENGTH: 18
<212> TYPE: DNA
<213> ORGANISM: Nicotiana tabacum

<400> SEQUENCE: 18
tgtaaaacga cggccagt                                                    18

<210> SEQ ID NO 19
<211> LENGTH: 18
<212> TYPE: DNA
<213> ORGANISM: Nicotiana tabacum

<400> SEQUENCE: 19
caggaaaccg atatgacc                                                    18

<210> SEQ ID NO 20
<211> LENGTH: 1103
<212> TYPE: DNA
<213> ORGANISM: Nicotiana tabacum

<400> SEQUENCE: 20
tcgattaaaa atcccaatta tatttgcaga ttaaatcaaa ccataactca ttttgtttaa      60
gcttggtttg gttttatatt tatataagtt tttatatata tgcctttaag acttttata     120
gaattttctt taaaaaatat ctagaaatat ttgcgactct tctggcatgt aatatttcgt    180
taaatatgaa gtgctccatt tttattaact ttaaataatt ggttgtacga tcactttctt    240
atcaagtgtt actaaaatgc gtcaatctct ttgttcttcc atattcatat gtcaaaatct    300
atcaaaattc ttatatatct ttttcgaatt tgaagtgaaa tttcgataat ttaaaattaa    360
atagaacata tcattattta ggtatcatat tgatttttat acttaattac taaatttggt    420
taactttgaa agtgtacatc aacgaaaaat tagtcaaacg actaaaataa ataaatatca    480
tgtgttatta agaaaattct cctataagaa tattttaata gatcatatgt ttgtaaaaaa    540
aattaatttt tactaacaca tatatttact tatcaaaaat ttggcaaaac cgaaccaatc    600
caaccgatat agttggtttg gtttgatttt gatataaacc gaaccaactc ggtccatttg    660
caccectaat cataatagct ttaatatttc aagatattat taagttaacg ttgtcaatat    720
cctggaaatt ttgcaaaatg aatcaagcct atatggctgt aatatgaatt taaaagcagc    780
tcgatgtggt ggtaatatgt aatttacttg attctaaaaa aatatcccaa gtattaataa    840
tttctgctag gaagaaggtt agctacgatt tacagcaaag ccagaataca agaaccata     900
aagtgattga agctcgaaat atacgaagga acaaatattt ttaaaaaaat acgcaatgac    960
ttggaacaaa agaaagtgat atatttttg ttcttaaaca agcatcccct ctaaagaatg    1020
gcagttttcc tttgcatgta actattatgc tcccttcgtt acaaaaattt tggactacta    1080
ttgggaactt cttctgaaaa tag                                           1103

<210> SEQ ID NO 21
<211> LENGTH: 838
<212> TYPE: DNA
<213> ORGANISM: Nicotiana tabacum

<400> SEQUENCE: 21
aagcttacat tttatgttag ctggtggact gacgccagaa aatgttggtg atgcgcttag      60
attaatggcg ttattggtgt tgatgtaagc ggaggtgtgg agacaaatgg tgtaaaagac    120
tctaacaaaa tagcaaattt cgtcaaaaat gctaagaaat aggttattac tgagtagtat    180
ttatttaagt attgtttgtg cacttgcctg caggccttt gaaaagcaag cataaaagat    240
ctaaacataa aatctgtaaa ataacaagat gtaaagataa tgctaaatca tttggctttt    300

-continued

```
tgattgattg tacaggaaaa tatacatcgc aggggggttga cttttaccat ttcaccgcaa      360
tggaatcaaa cttgttgaag agaatgttca caggcgcata cgctacaatg acccgattct      420
tgctagcctt ttctcggtct tgcaaacaac cgccggcagc ttagtatata aatacacatg      480 tacataccc  tctccgtatc ctcgtaatca ttttcttgta tttatcgtct tttcgctgta      540
aaaactttat cacacttatc tcaaatacac ttattaaccg cttttactat tatcttctac      600
gctgacagta atatcaaaca gtgacacata ttaaacacag tggtttcttt gcataaacac      660
catcagcctc aagtcgtcaa gtaaagattt cgtgttcatg cagatagata acaatctata      720
tgttgataat tagcgttgcc tcatcaatgc gagatccgtt taaccggacc ctagtgcact      780
taccccacgt tcggtccact gtgtgccgaa catgctcctt cactatttta acatgtgg       838
```

<210> SEQ ID NO 22
<211> LENGTH: 9
<212> TYPE: DNA
<213> ORGANISM: Nicotiana tabacum

<400> SEQUENCE: 22 aatatattt                                                              9